(12) United States Patent
Tada et al.

(10) Patent No.: US 8,986,858 B2
(45) Date of Patent: Mar. 24, 2015

(54) ORGANIC ELECTROLUMINESCENT DEVICE

(75) Inventors: Masashi Tada, Kitakyushu (JP); Junya Ogawa, Kitakyushu (JP); Takahiro Kai, Kitakyushu (JP); Megumi Matsumoto, Kitakyushu (JP); Yasuhisa Tsutsumi, Tokyo (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 402 days.

(21) Appl. No.: 13/578,942

(22) PCT Filed: Jan. 27, 2011

(86) PCT No.: PCT/JP2011/051640
§ 371 (c)(1),
(2), (4) Date: Aug. 14, 2012

(87) PCT Pub. No.: WO2011/105161
PCT Pub. Date: Sep. 1, 2011

(65) Prior Publication Data
US 2012/0319095 A1    Dec. 20, 2012

(30) Foreign Application Priority Data
Feb. 26, 2010  (JP) .................................. 2010-042295

(51) Int. Cl.
*H01L 51/50* (2006.01)
*C07D 403/10* (2006.01)
(Continued)

(52) U.S. Cl.
CPC ............ *C07D 403/10* (2013.01); *C07D 209/86* (2013.01); *C07D 401/14* (2013.01);
(Continued)

(58) Field of Classification Search
None
See application file for complete search history.

(56) References Cited

U.S. PATENT DOCUMENTS 7,829,204 B2   11/2010  Iwakuma et al.
2005/0175858 A1  8/2005  Jung et al.

FOREIGN PATENT DOCUMENTS

EP    1 962 354 A1    8/2008
JP    2004-071500  *  3/2004  ............ C09K 11/06
(Continued)

OTHER PUBLICATIONS

International Preliminary Report on Patentability for Application No. PCT/JP2011/051640 mailed Oct. 26, 2012.
(Continued)

*Primary Examiner* — Gregory Clark
(74) *Attorney, Agent, or Firm* — Cheng Law Group, PLLC

(57) ABSTRACT

Disclosed is an organic electroluminescent device (organic EL device) that is improved in luminous efficiency, sufficiently secures driving stability, and has a simple configuration. This organic EL device comprises organic layers between an anode and a cathode piled one upon another on a substrate and at least one organic layer selected from a light-emitting layer, a hole-transporting layer, an electron-transporting layer, and a hole-blocking layer contains a carbazole compound represented by the following formula (1). In the case where the light-emitting layer of the organic electroluminescent device contains a phosphorescent dopant and a host material, it is the carbazole compound that is contained as the host material. In formula (1), X is C—Y or a nitrogen atom; Y is a hydrogen atom, an alkyl group, a cycloalkyl group, or an aromatic group; n is an integer of 2 to 4: A is an n-valent aromatic group; L is a direct bond or a divalent aromatic group; and R is a hydrogen atom, an alkyl group, or a cycloalkyl group.

4 Claims, 2 Drawing Sheets

(51) Int. Cl.
*C07D 209/86* (2006.01)
*C07D 401/14* (2006.01)
*C07D 403/14* (2006.01)
*C07D 405/14* (2006.01)
*C07D 409/14* (2006.01)
*H01L 51/00* (2006.01)

(52) U.S. Cl.
CPC ............ *C07D403/14* (2013.01); *C07D 405/14* (2013.01); *C07D 409/14* (2013.01); *H01L 51/0067* (2013.01); *H01L 51/0072* (2013.01); *H01L 51/0073* (2013.01); *H01L 51/0074* (2013.01); *H01L 51/0087* (2013.01); *H01L 51/5016* (2013.01); *H01L 51/5048* (2013.01); *H01L 51/5096* (2013.01); *Y10S 428/917* (2013.01)
USPC ........... 428/690; 428/917; 313/504; 313/505; 313/506; 257/40; 257/E51.05; 257/E51.026; 257/E51.032; 548/304.1; 548/418; 548/440; 548/444; 546/18; 546/24; 544/234

(56) References Cited

FOREIGN PATENT DOCUMENTS

| | | |
|---|---|---|
| JP | 2004-71500 A | 3/2004 |
| JP | 2004-342391 A | 12/2004 |
| JP | 2005-93159 A | 4/2005 |
| JP | 2009-114370 A | 5/2009 |
| JP | 2009-170817 A | 7/2009 |
| JP | 2009-263579 | 11/2009 |
| WO | WO-2009/104488 A1 | 8/2009 |

OTHER PUBLICATIONS

International Search Report for the Application No. PCT/JP2011/051640 mailed Apr. 12, 2011.

* cited by examiner

ORGANIC ELECTROLUMINESCENT DEVICE

TECHNICAL FIELD

This invention relates to an organic electroluminescent device material for use in an organic electroluminescent device and an organic electroluminescent device using the material and, more particularly, to a thin film type device that emits light upon application of an electric field to a light-emitting layer composed of an organic compound.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent years, studies have been started to develop organic EL devices in which organic thin films are used. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been directed toward practical applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. However, the utilization of phosphorescence, that is, emission of light from the triplet excited state, is expected to enhance the luminous efficiency three to four times that of the conventional devices utilizing fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they too failed to emit light at high efficiency. In recent years, as stated in patent document 1, a large number of researches are conducted on phosphorescent dopant materials, with a focus on the use of organic metal complexes such as iridium complexes, for the purpose of enhancing the luminous efficiency and extending the life.

PRIOR ART TECHNICAL DOCUMENTS

Patent Documents

Patent document 1: JP 2005-093159 A
Patent document 2: WO 2005-057987
Patent document 3: JP2005-132820 A
Patent document 4: JP2004-071500 A In order to obtain high luminous efficiency, a host material to be used together with the aforementioned dopant material becomes important. Of the host materials proposed thus far, a typical example is 4,4'-bis(9-carbazolyl)biphenyl (hereinafter referred to as CBP) presented in patent document 2. Since CBP is characterized by having a good hole transfer property but a poor electron transfer property, the use of CBP as a host material for tris(2-phenylpyridine)iridium complex (hereinafter referred to as Ir(ppy)$_3$), a typical phosphorescent green light-emitting material, disturbs the balanced injection of electric charges and causes excessive holes to flow out to the side of the electron-transporting layer. The result is a reduction in the luminous efficiency of Ir(ppy)$_3$.

As described above, in order for an organic EL device to display high luminous efficiency, a host material that has high triplet excitation energy and is well balanced in the injection and transport characteristics of electric charges (holes and electrons) is required. Furthermore, compounds that are electrochemically stable, highly resistant to heat, and excellently stable in the amorphous state are desired and further improvements are demanded.

Patent document 1 discloses the carbazole compound illustrated below as a host material for an organic EL device.

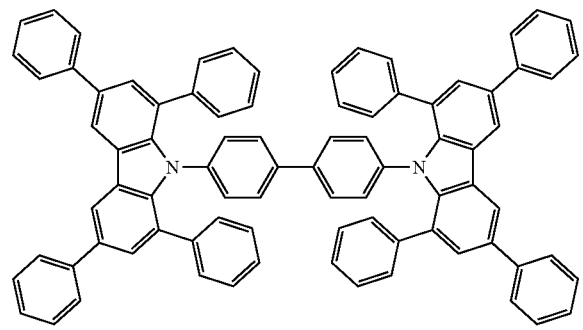 [SMILES: c1ccc(-c2cc(-c3ccccc3)c3c(c2)c2cc(-c4ccccc4)cc(-c4ccccc4)c2n3-c2ccc(-c3ccc(-n4c5c(-c6ccccc6)cc(-c6ccccc6)cc5c5cc(-c6ccccc6)cc(-c6ccccc6)c54)cc3)cc2)cc1]

However, it is conjectured that sufficient luminous efficiency cannot be obtained from this carbazole compound because each carbazole moiety in the compound has phenyl groups at the positions 3 and 6.

Patent document 2 discloses the carbazole compound illustrated below as a host material for an organic EL device.

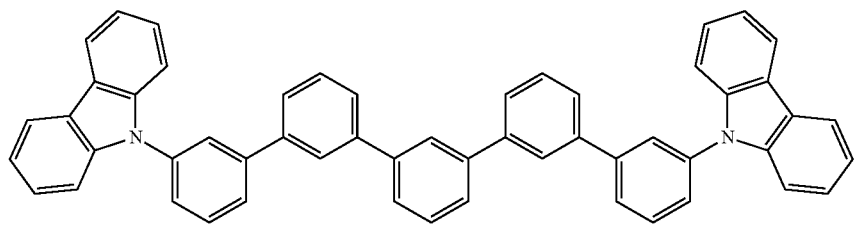 [SMILES: c1cc(-c2cccc(-c3cccc(-n4c5ccccc5c5ccccc54)c3)c2)cc(-c2cccc(-c3cccc(-n4c5ccccc5c5ccccc54)c3)c2)c1]

Patent document 3 discloses the carbazole compound illustrated below as a host material for an organic EL device.

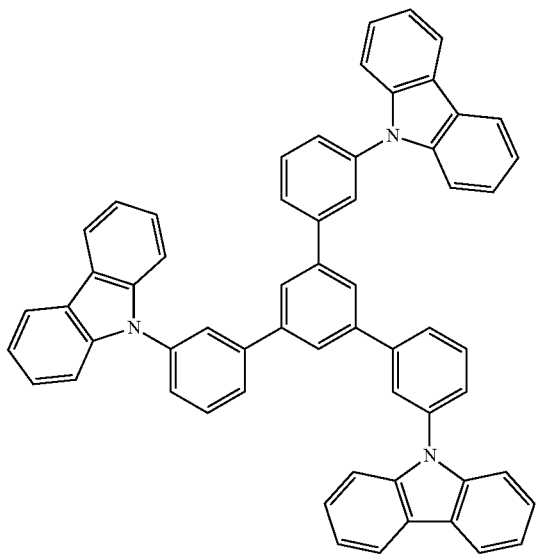 [SMILES: c1cc(-c2cc(-c3cccc(-n4c5ccccc5c5ccccc54)c3)cc(-c3cccc(-n4c5ccccc5c5ccccc54)c3)c2)cc(-n2c3ccccc3c3ccccc32)c1]

However, the aforementioned documents merely disclose compounds in which each carbazole moiety is linked at the position 9 to the linking group and by no means disclose the usefulness of an organic EL device using a compound in which each carbazole moiety is linked at the position 1 to the linking group.

Patent document 4 discloses the carbazole compound illustrated below as a host material for an organic EL device.

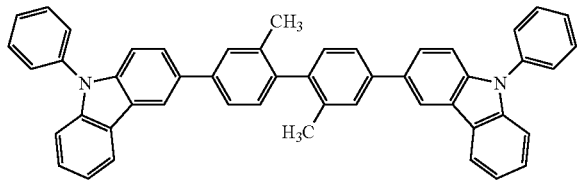 [SMILES: Cc1cc(-c2ccc3c(c2)c2ccccc2n3-c2ccccc2)ccc1-c1ccc(-c2ccc3c(c2)c2ccccc2n3-c2ccccc2)cc1C]

However, the aforementioned document merely discloses a compound in which each carbazole moiety is linked at the position 3 to the linking group and by no means discloses the usefulness of an organic EL device using a compound in which each carbazole moiety is linked at the position 1 to the linking group.

DISCLOSURE OF THE INVENTION

In applications of organic EL devices to display devices such as flat panel displays, it is necessary to enhance the luminous efficiency of the device and, at the same time, to sufficiently secure the driving stability of the device. Under the aforementioned circumstances, an object of this invention is to provide an organic EL device exhibiting such luminous efficiency and driving stability as to be practically useful and to provide a compound suitable therefor.

The inventors of this invention have conducted intensive studies, found that the use of a carbazole compound composed of two or more carbazole rings linked together via a linking group, each carbazole ring being linked at the position 1 to the linking group and having a specified substituent at the position 9, in an organic EL device enables the device to display excellent characteristics, and completed this invention.

This invention relates to an organic electroluminescent device comprising an anode, organic layers, and a cathode piled one upon another on a substrate wherein at least one layer selected from the group consisting of a light-emitting layer, a hole-transporting layer, an electron-transporting layer, and a hole-blocking layer contains a carbazole compound represented by general formula (1).

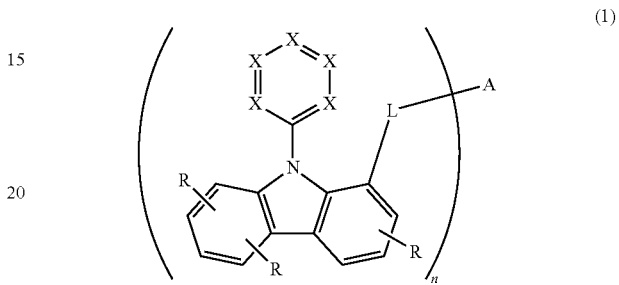

(1)

In general formula (1), each X is independently C—Y or a nitrogen atom and each Y is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 18 carbon atoms; n is an integer of 2 to 4; A is an n-valent aromatic hydrocarbon group of 6 to 50 carbon atoms or an n-valent aromatic heterocyclic group of 3 to 50 carbon atoms; each L is independently a direct bond, a divalent non-fused ring aromatic hydrocarbon group of 6 to 10 carbon atoms, or a divalent non-fused ring aromatic heterocyclic group of 3 to 10 carbon atoms; each R is independently a hydrogen atom, an alkyl group of 1 to 10 carbon atoms, or a cycloalkyl group of 3 to 11 carbon atoms; in the case where L is a direct bond, A cannot have a fused ring structure.

In general formula (1), L is preferably a direct bond, a divalent five- or six-membered aromatic hydrocarbon group, or a divalent five- or six-membered aromatic heterocyclic group; more preferably, L is a direct bond, a phenylene group, or a divalent six-membered aromatic heterocyclic group. Further, in general formula (1), n is an integer of 2 to 4, preferably 2 or 3.

Moreover, it is preferable that the aforementioned organic electroluminescent device comprises a light-emitting layer containing a carbazole compound represented by general formula (1) and a phosphorescent dopant.

A carbazole compound represented by general formula (1) has two or more carbazole skeletons linked together via a linking group, each carbazole skeleton having monocyclic aromatic groups as substituents at the positions 1 and 9 while the monocyclic aromatic group at the position 1 acting as a linking group. It is conceivable that this specific structure of the compound makes it possible to adjust finely the transfer rates of holes and electrons and control the values of a variety of energies such as ionization potential (IP), electron affinity (EA), and triplet excitation energy (T1). Further, this carbazole compound is considered to have a potentiality to improve the stability in various activated states such as oxidation, reduction, and excitation and, at the same time, it has good characteristics in the amorphous state. The aforementioned properties are able to realize organic EL devices of long driving life and high durability.

PREFERRED EMBODIMENTS OF THE INVENTION

Figure 1:
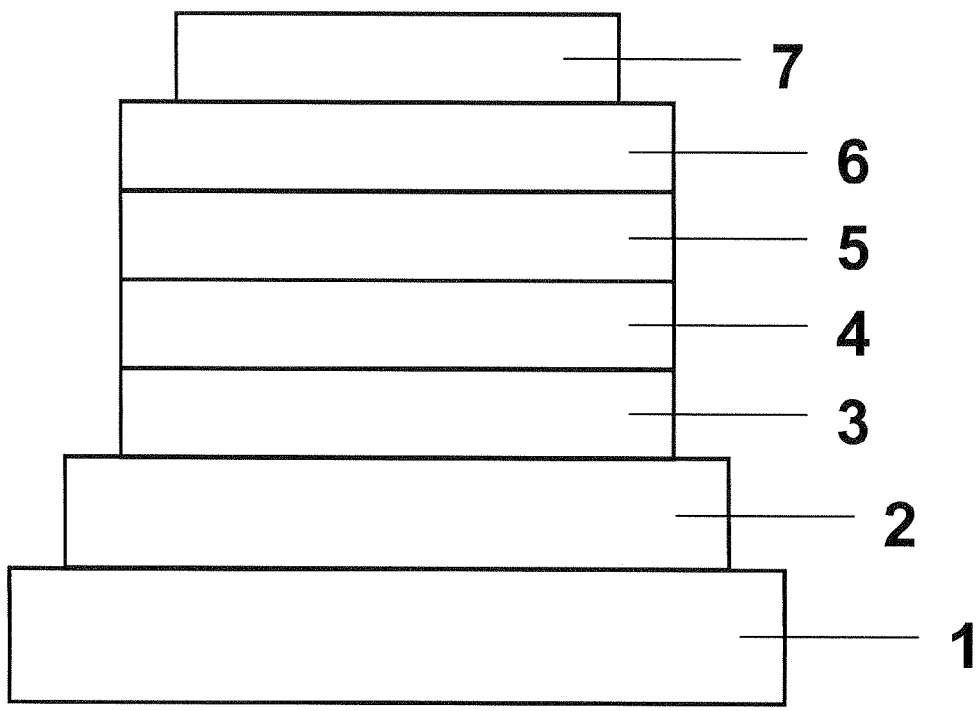
FIG. 1 is the cross section to illustrate an example of the structure of an organic EL device.

An organic electroluminescent device according to this invention contains a carbazole compound represented by the aforementioned general formula (1) in a specified layer. In general formula (1), n is an integer of 2 to 4 and A is an n-valent aromatic hydrocarbon group of 6 to 50 carbon atoms or an n-valent aromatic heterocyclic group of 3 to 50 carbon atoms. That is, a carbazole compound represented by general formula (1) has a structure in which the n number of carbazole-containing groups are linked to the n-valent group A.

In general formula (1), each X is independently C—Y or a nitrogen atom and Y is a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms. In the case where a plurality of Ys exist, they may be identical with or different from one another.

In general formula (1), each X is independently C—Y or a nitrogen atom and when X is a nitrogen atom, the number of nitrogen atoms is preferably 1 to 3, more preferably 1 or 2.

In the case where X is C—Y in general formula (1), each Y is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; preferably a hydrogen atom, an alkyl group of 1 to 6 carbon atoms, a cycloalkyl group of 3 to 8 carbon atoms, an aromatic hydrocarbon group of 6 to 14 carbon atoms, or an aromatic heterocyclic group of 3 to 13 carbon atoms. In the case where Y is an aromatic hydrocarbon group or an aromatic heterocyclic group, the group Y preferably has a non-fused ring structure.

Examples of the alkyl group and the cycloalkyl group include a methyl group, an ethyl group, a propyl group, a butyl group, a pentyl group, a hexyl group, a heptyl group, an octyl group, a nonyl group, a decyl group, a cyclohexyl group, and a methylcyclohexyl group and it does not matter whether the group is linear or branched. Preferable examples include alkyl groups of 1 to 6 carbon atoms, a cyclohexyl group, and a methylcyclohexyl group; specifically, they include a methyl group, an ethyl group, a propyl group, a butyl group, a pentyl group, a hexyl group, a cyclohexyl group, and a methylcyclohexyl group.

Examples of the aromatic hydrocarbon group and the aromatic heterocyclic group include monovalent groups formed by removing a hydrogen atom from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, phenanthroline, phenazine, benzofuran, dibenzofuran, xanthene, oxanthrene, phenoxazine, benzothiophene, dibenzothiophene, thioxanthene, thianthrene, phenoxathiine, and phenothiazine or from compounds in which a plurality of these aromatic rings are linked together. Examples of the monovalent groups derived from the aforementioned aromatic compounds in which a plurality of the aromatic rings are linked together include monovalent groups formed by removing a hydrogen atom from biphenyl, terphenyl, bipyridine, bipyrimidine, bitriazine, bistriazylbenzene, binaphthelene, phenylpyridine, diphenylpyridine, diphenylpyrimidine, diphenyltriazine, phenylcarbazole, and pyridylcarbazole. The position of linkage of the group consisting of linked aromatic rings is not limited and it does not matter whether linkage occurs in a ring at the end or in a ring in the middle.

Preferable examples of the aromatic hydrocarbon group and the aromatic heterocyclic group include monovalent groups formed by removing a hydrogen atom from benzene, pyridine, pyrimidine, triazine, carbazole, dibenzofuran, oxanthrene, phenoxazine, dibenzothiophene, thianthrene, and phenothiazine or from aromatic compound in which a plurality of these aromatic rings are linked together. More preferable examples include monovalent groups formed by removing a hydrogen atom from benzene, pyridine, pyrimidine, triazine, dibenzofuran, and dibenzothiophene or from aromatic compound in which a plurality of these aromatic rings are linked together.

In general formula (1), each of a plurality of Rs is independently a hydrogen atom, an alkyl group of 1 to 10 carbon atoms, or a cycloalkyl group of 3 to 11 carbon atoms, preferably a hydrogen atom, an alkyl group of 1 to 6 carbon atoms, or a cycloalkyl group of 3 to 8 carbon atoms. Examples of the alkyl group and the cycloalkyl group include a methyl group, an ethyl group, a propyl group, a butyl group, a pentyl group, a hexyl group, a heptyl group, an octyl group, a nonyl group, a decyl group, a cyclohexyl group, and a methylhexyl group. Preferable examples of R include a hydrogen atom, a methyl group, an ethyl group, a propyl group, a butyl group, a pentyl group, a hexyl group, a cyclohexyl group, and a methylcyclohexyl group and a more preferable example is a hydrogen atom.

In general formula (1), n is an integer of 2 to 4, preferably 2 or 3, more preferably 2.

In general formula (1), A is an n-valent aromatic hydrocarbon group of 6 to 50 carbon atoms or an n-valent aromatic heterocyclic group of 3 to 50 carbon atoms, preferably an n-valent aromatic hydrocarbon group of 6 to 36 carbon atoms or an n-valent aromatic heterocyclic group of 3 to 36 carbon atoms In the case where A is an aromatic hydrocarbon group or an aromatic heterocyclic group, examples thereof include n-valent groups formed by removing the n number of hydrogen atoms from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, phenanthroline, phenazine, benzofuran, dibenzofuran, xanthene, oxanthrene, phenoxazine, benzothiophene, dibenzothiophene, thioxanthene, thianthrene, phenoxathiine, and phenothiazine or from aromatic compounds in which a plurality of these aromatic rings are linked together. Preferable examples include n-valent groups formed by removing the n number of hydrogen atoms from benzene, naphthalene, fluorene, anthracene, phenanthrene, fluoranthene, pyrene, chrysene, pyridine, pyrimidine, triazine, indole, quinoline, isoquinoline, quinoxaline, naphthyridine, carbazole, acridine, benzofuran, dibenzofuran, phenoxazine, benzothiophene, dibenzothiophene, and phenothiazine or from aromatic compounds in which a plurality of these aromatic rings are linked together. More preferable example include n-valent groups formed by removing n hydrogen atoms from benzene, pyridine, pyrimidine, triazine, carbazole, dibenzofuran, and dibenzothiophene or from aromatic compounds in which a plurality of these aromatic rings are linked together. In the case where a plurality of the aforementioned aromatic rings are linked together, they may be identical with or different from one another. Examples of n-valent groups derived from the aforementioned aromatic compounds in which a plurality of aromatic rings are linked together include n-valent groups formed by removing the n number of hydrogen atoms from biphenyl, terphenyl, bipyridine, bipyrimidine, bitriazine, bistriazylbenzene, binaphthalene, phenylpyridine, diphenylpyridine, diphenylpyrimidine, diphenyltriazine, phenylcarbazole, and pyridylcarbazole. The position of linkage of A to L or to the position 1 of carbazole is not limited and it does not matter whether linkage occurs in a ring at the end or in a ring in the middle. The aforementioned aromatic hydrocarbon groups or aromatic heterocyclic groups may have substituents. When the groups have substituents, preferable examples thereof include an alkyl group of 1 to 4 carbon atoms, a cycloalkyl group of 3 to 6 carbon atoms, an alkoxyl group of 1 to 2 carbon groups, an acetyl group, and a diarylamino group of 6 to 24 carbon atoms. In the aforementioned case where the groups have substituents, the total number of substituents is 1 to 10, preferably 1 to 6, more preferably 1 to 4. Further, in the case where 2 or more substituents are present, they may be identical with or different from one another. In counting the number of carbon atoms in the aforementioned aromatic hydrocarbon groups or aromatic heterocyclic groups having substituents, the number of carbon atoms in the substituents is included.

In the case where the groups derived from the aromatic compounds in which a plurality of aromatic rings are linked together are divalent, such divalent groups are represented, for example, by the following formulas.

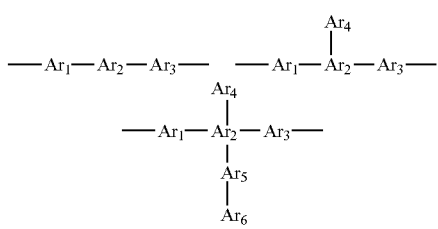

(The groups $Ar_1$ to $Ar_6$ are aromatic rings.)

In the case where L is a direct bond in general formula (1), A is an n-valent non-fused ring aromatic hydrocarbon group or an n-valent non-fused ring aromatic heterocyclic group. Here, "being a non-fused ring" when A is composed of a plurality of aromatic rings linked together means that an aromatic ring linking first to the n number of carbazole rings respectively at the position 1 in general formula (1) cannot have a fused ring structure. It does not matter if an aromatic ring other than the one linking first to the carbazole rings is a fused ring. However, A is preferably an n-valent group having a monocyclic ring structure or a structure formed by linking a plurality of monocyclic rings.

In general formula (1), L is a direct bond, a divalent non-fused ring aromatic hydrocarbon group of 6 to 10 carbon atoms, or a divalent non-fused ring aromatic heterocyclic group of 3 to 10 carbon atoms; preferably, a direct bond, a divalent five- or six-membered aromatic hydrocarbon group, or a divalent five- or six-membered aromatic heterocyclic group; more preferably a direct bond, a phenylene group, or a divalent six-membered aromatic heterocyclic group. Examples of the aromatic hydrocarbon group and the aromatic heterocyclic group include divalent groups formed by removing 2 hydrogen atoms from pyrrole, imidazole, furan, thiophene, oxazole, thiazole, pyrazole, benzene, pyridine, pyrimidine, pyrazine, pyridazine, and triazine. Preferable examples include divalent groups formed by removing 2 hydrogen atoms from benzene, pyrrole, furan, thiophene, pyridine, pyrimidine, and triazine. More preferable examples include divalent groups formed by removing 2 hydrogen atoms from benzene, pyridine, pyrimidine, and triazine. The aforementioned divalent aromatic hydrocarbon groups and aromatic heterocyclic groups may have substituents. When they have substituents, preferable examples thereof include an alkyl group of 1 to 4 carbon atoms, a cycloalkyl group of 3 to 6 carbon atoms, an alkoxyl group of 1 to 2 carbon atoms, and an acetyl group.

In general formula (1), groups preferred as A are formed by removing the n number of hydrogen atoms from the aromatic compounds illustrated below. In the case where the aromatic compound of choice has a structure formed by linking a monocyclic ring and a fused ring together, A is preferably a group formed by removing the n number of hydrogen atoms from the monocyclic ring. The aforementioned aromatic compounds may have substituents. When they have substituents, preferable examples thereof include an alkyl group of 1 to 4 carbon atoms, a cycloalkyl group of 3 to 6 carbon atoms, an alkoxyl group of 1 to 2 carbon atoms, and an acetyl group.

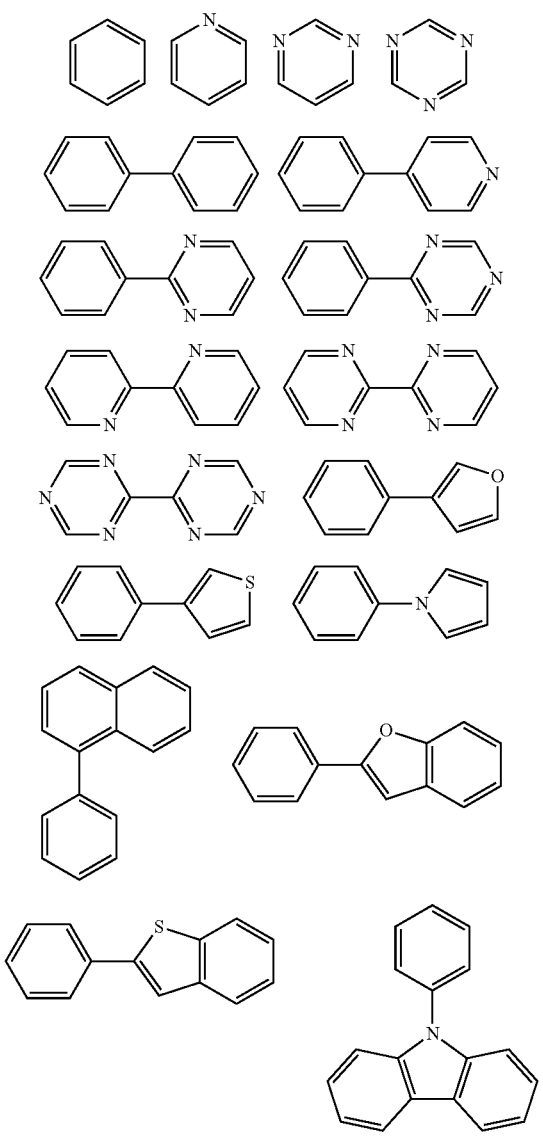

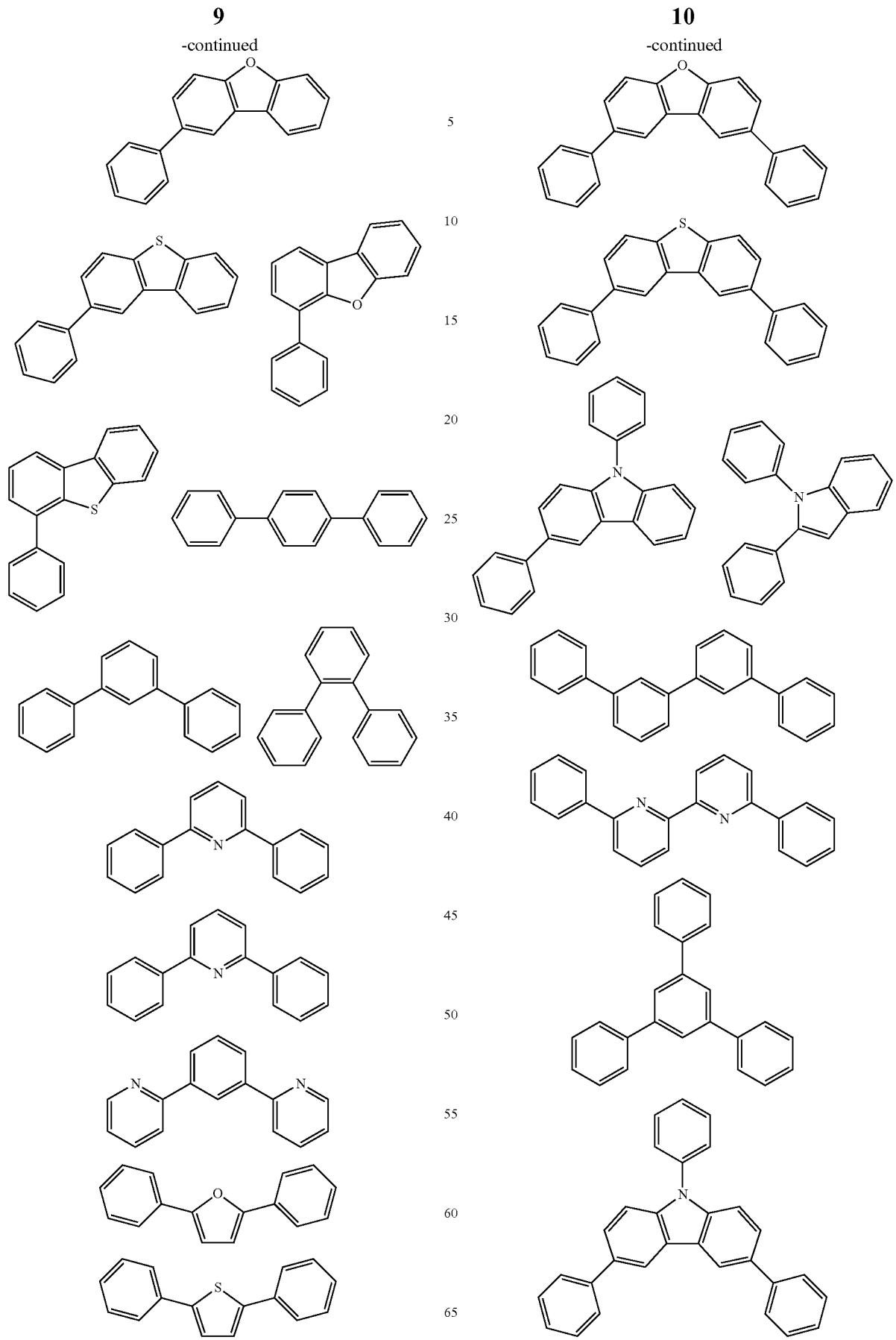

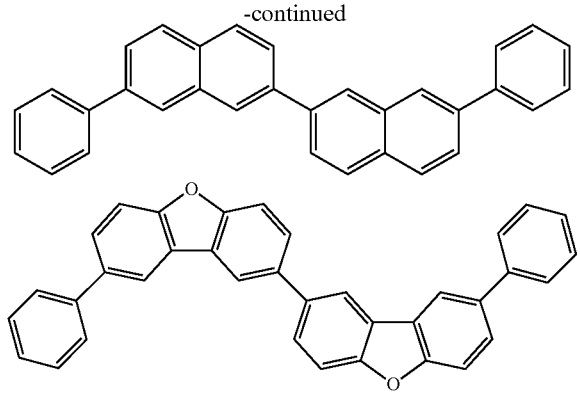
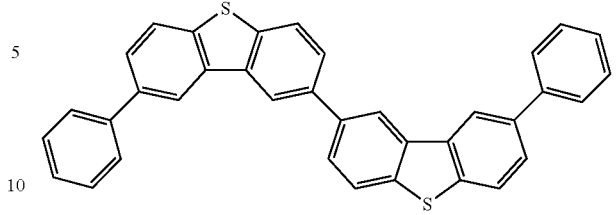
Specific examples of the carbazole compounds represented by general formula (1) are illustrated below, but are not limited thereto.
A-1
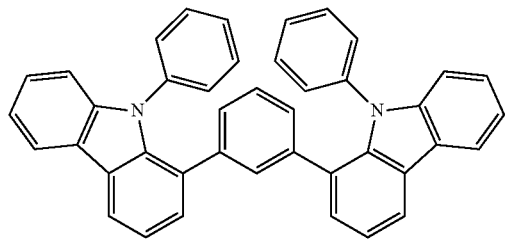
A-2
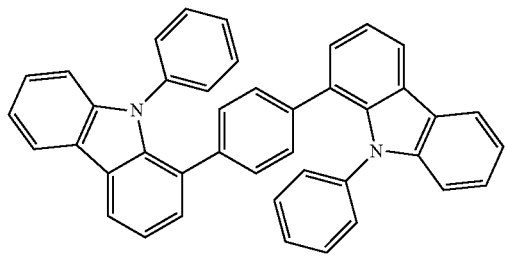
A-3
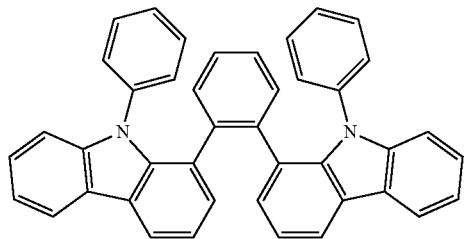
A-4
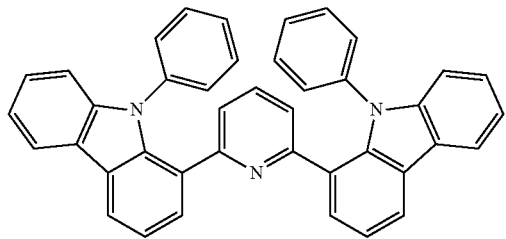
A-5
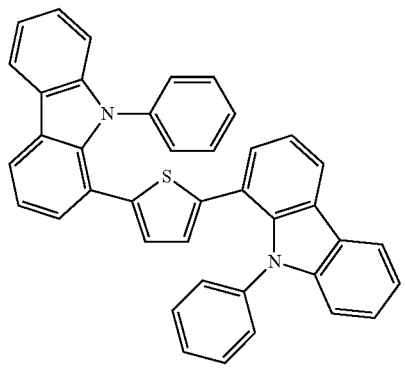
A-6
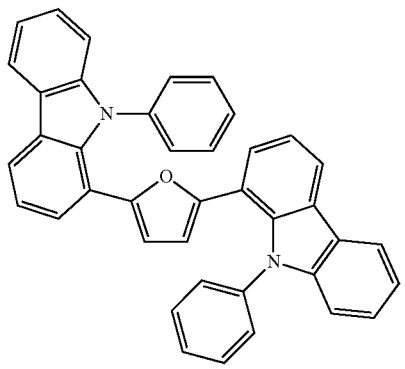

-continued
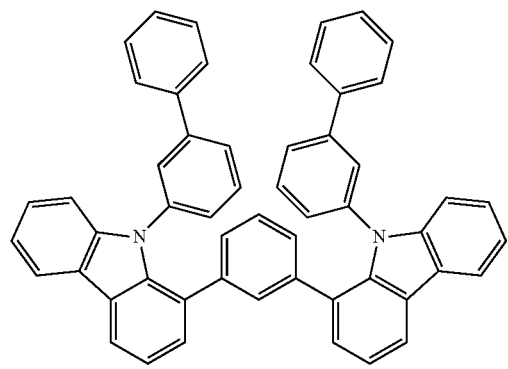
A-7
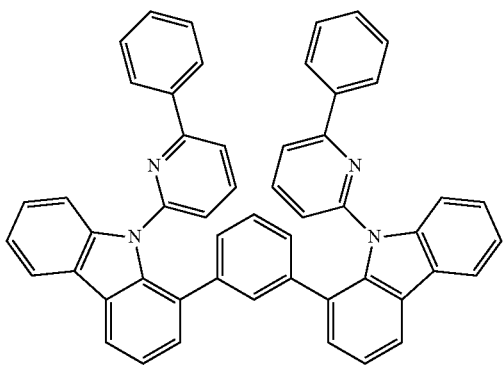
A-8
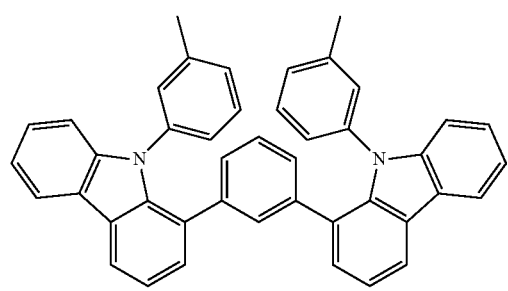
A-9
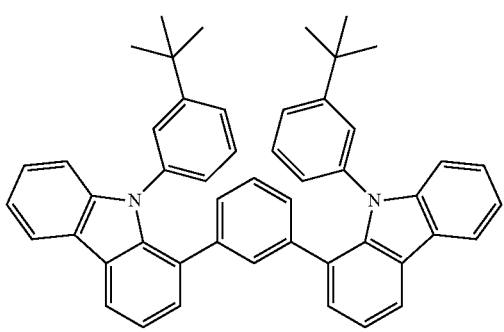
A-10
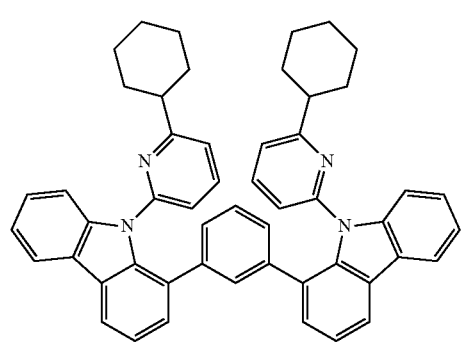
A-11
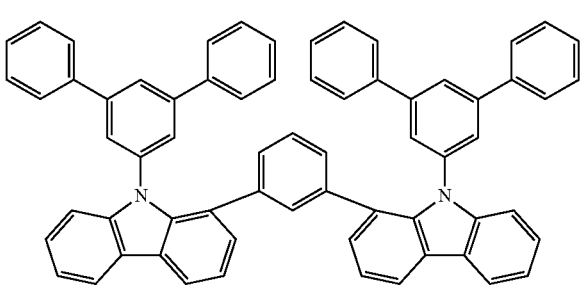
A-12
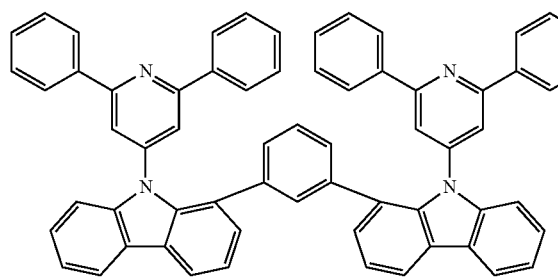
A-13
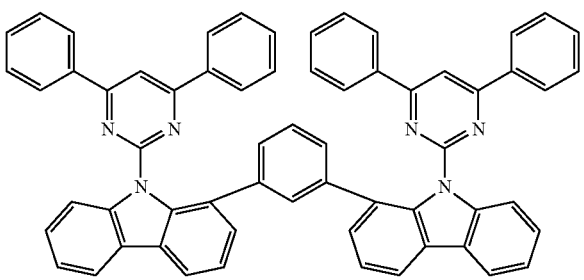
A-14

-continued
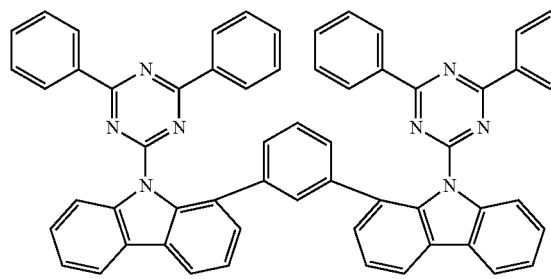
A-15
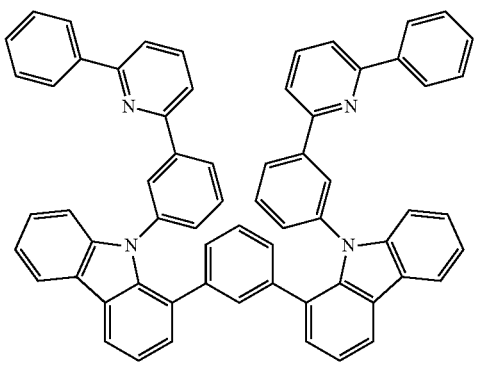
A-16
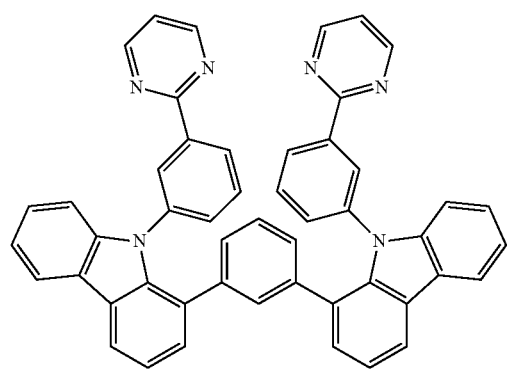
A-17
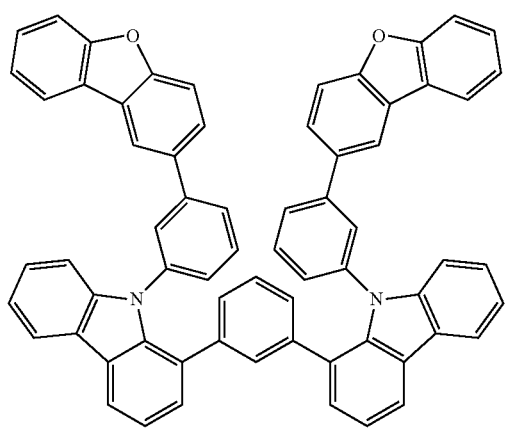
A-18
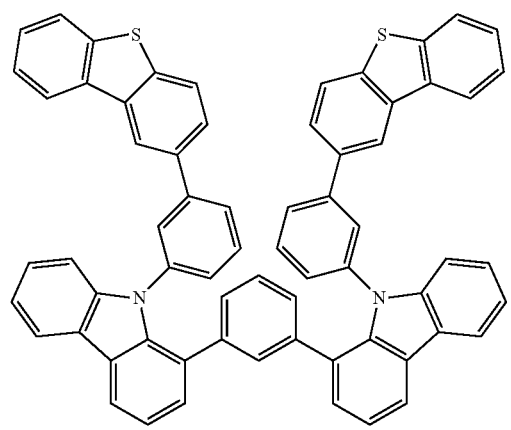
A-19
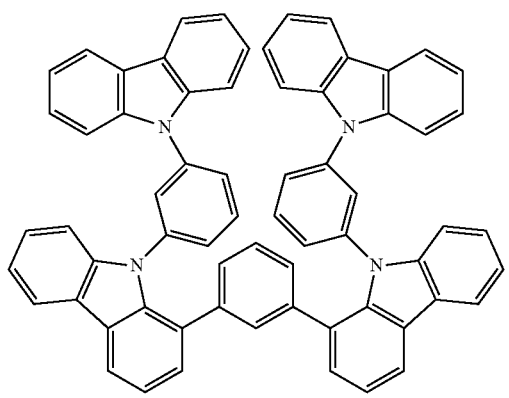
A-20

-continued
A-21
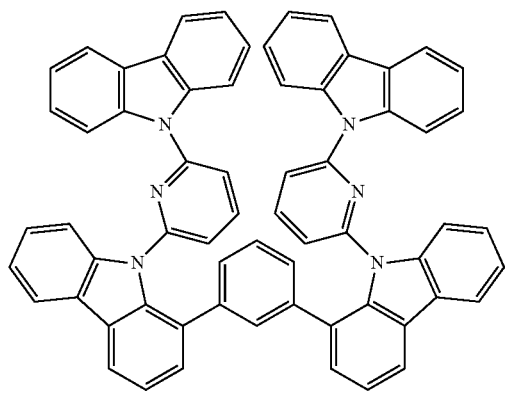
A-22
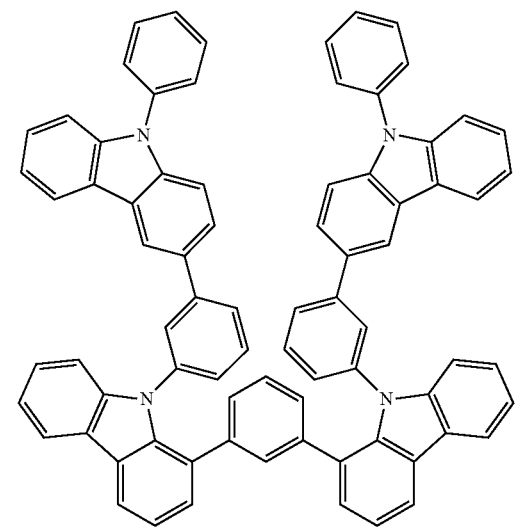
B-1
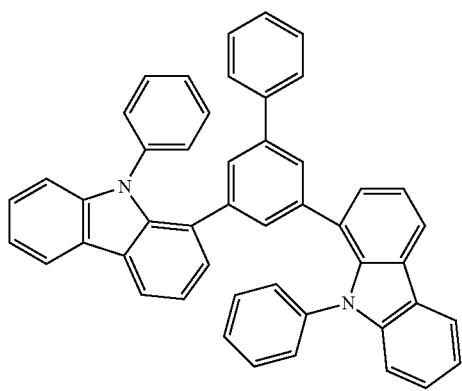
B-2
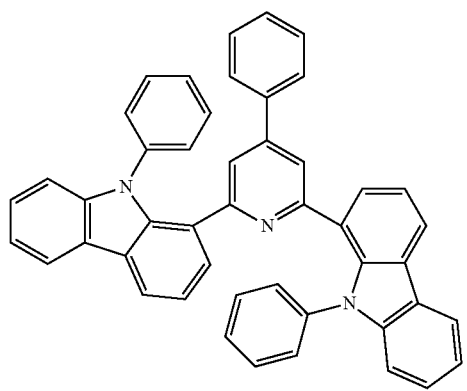
B-3
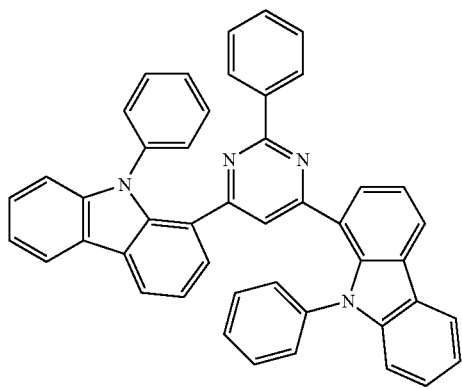
B-4
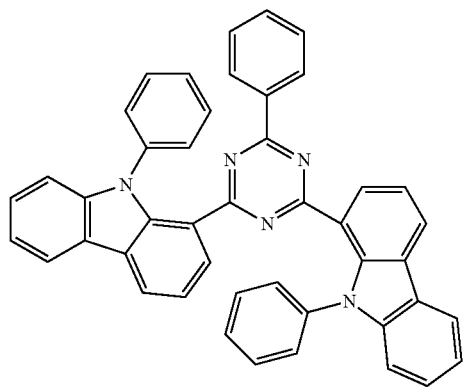

-continued
B-5
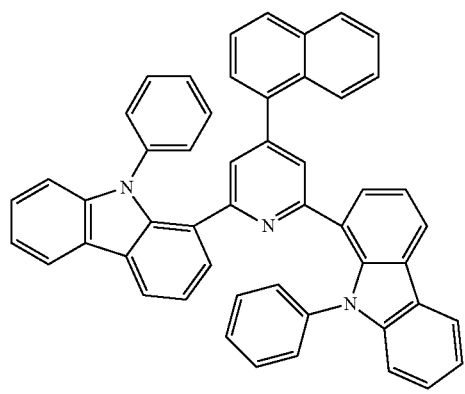
B-6
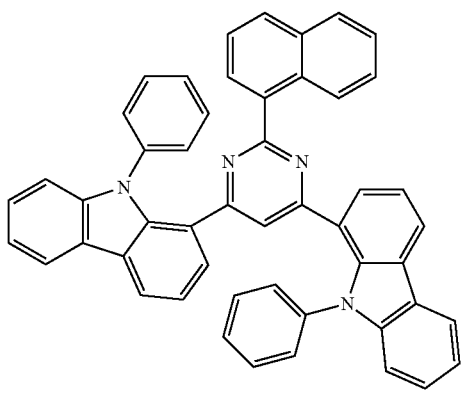
B-7
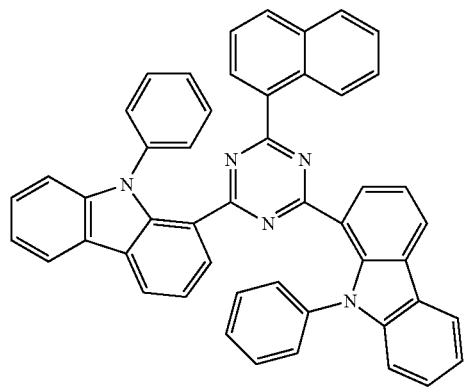
B-8
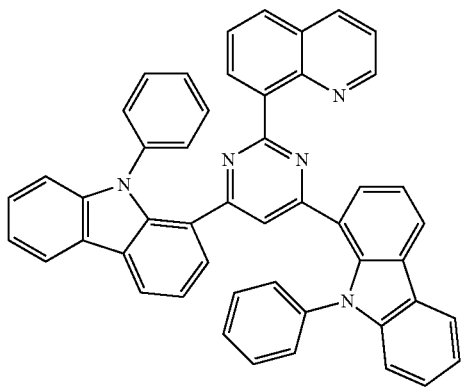
B-9
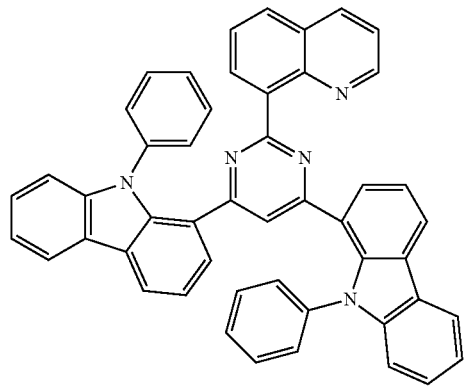
B-10
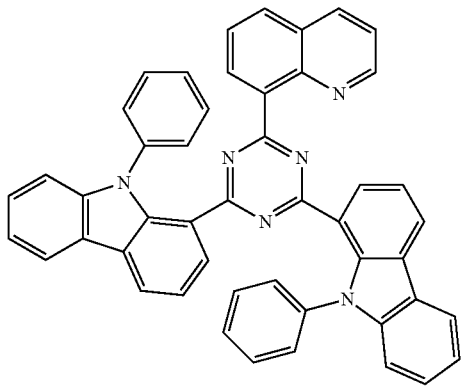
B-11
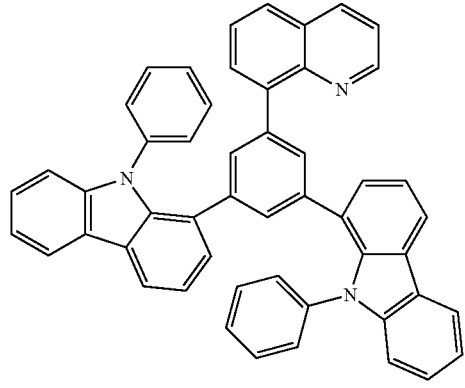
B-12
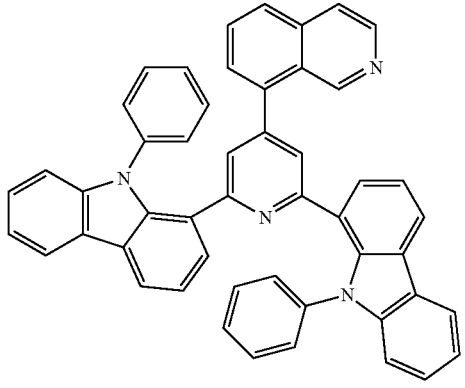

-continued
B-13
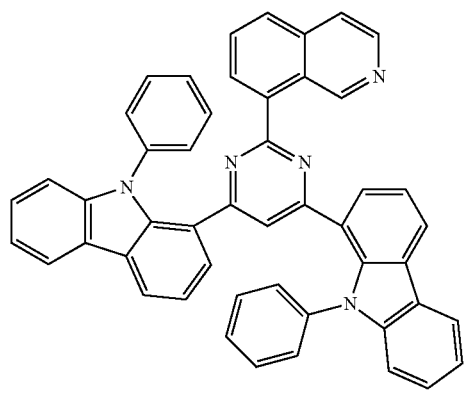
B-14
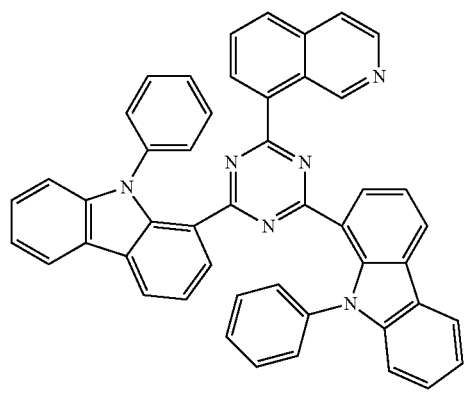
B-15
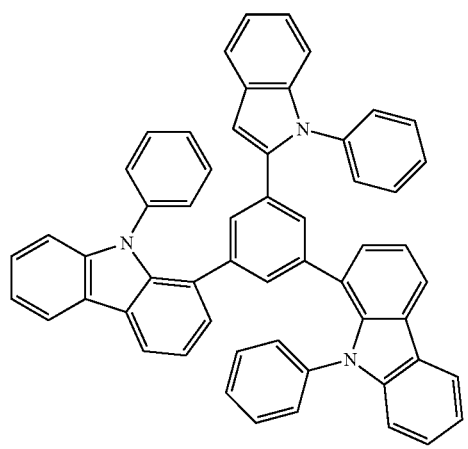
B-16
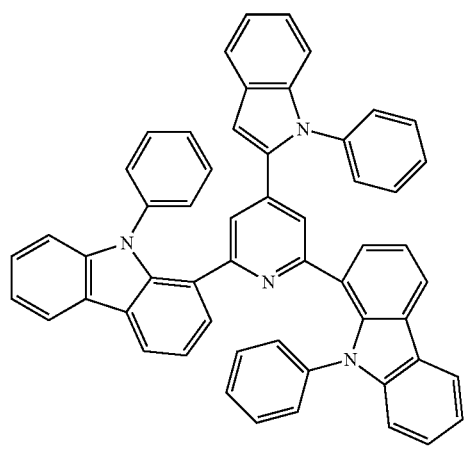
B-17
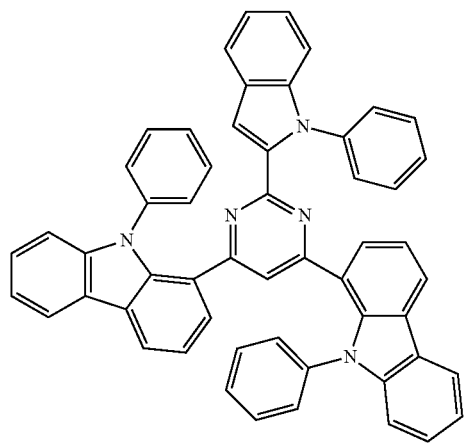
B-18
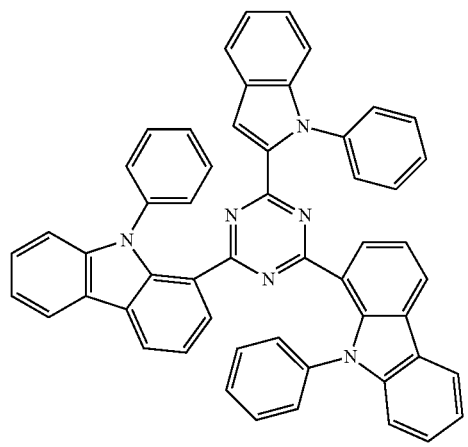

-continued
B-19
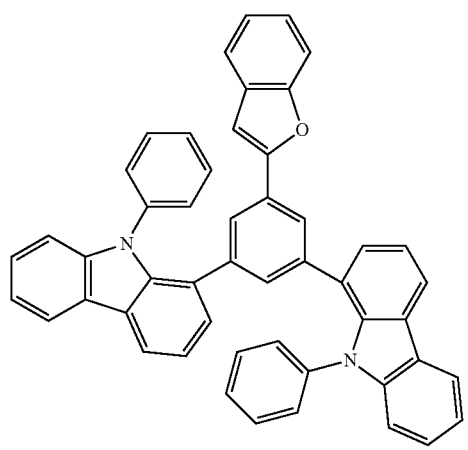
B-20
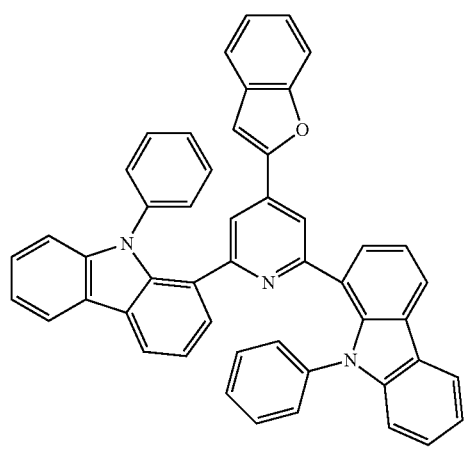
B-21
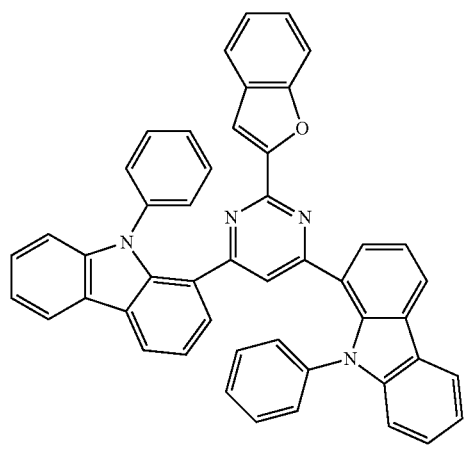
B-22
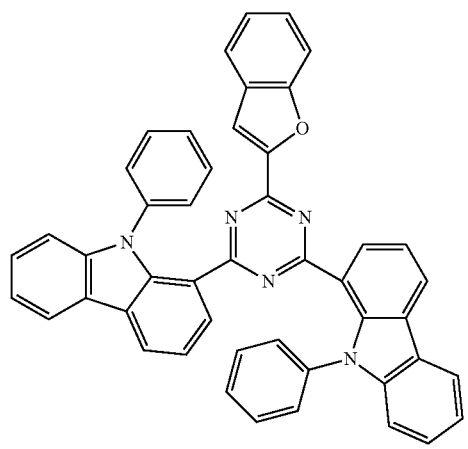
B-23
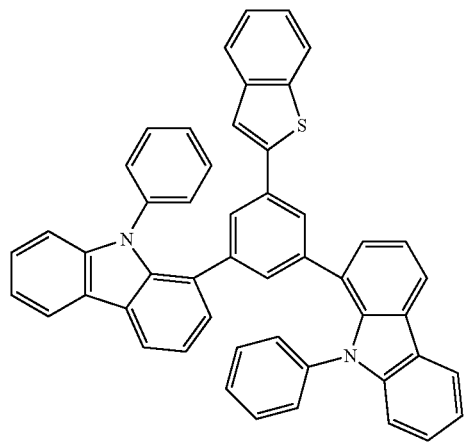
B-24
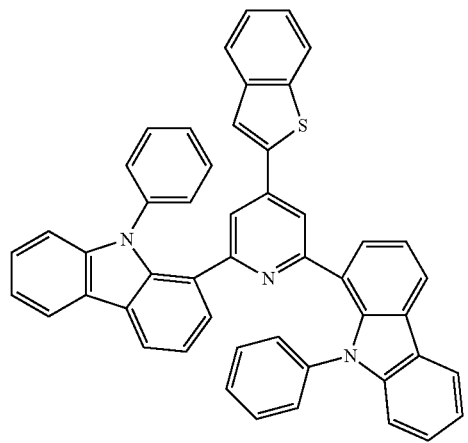

-continued
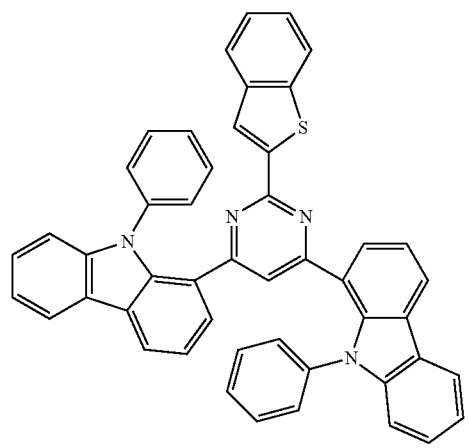
B-25
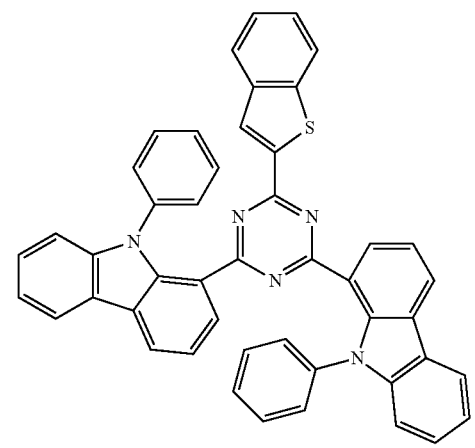
B-26
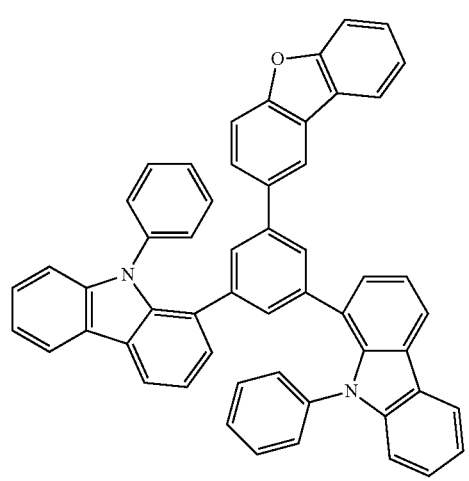
B-27
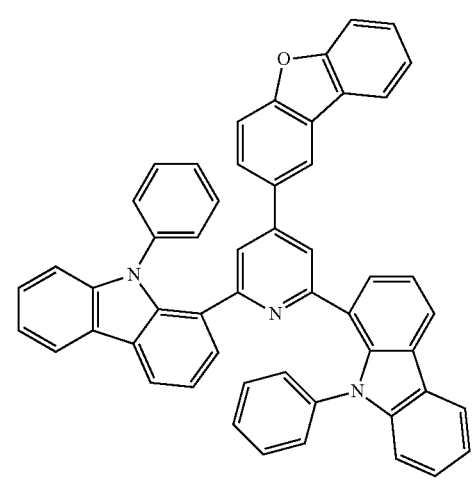
B-28
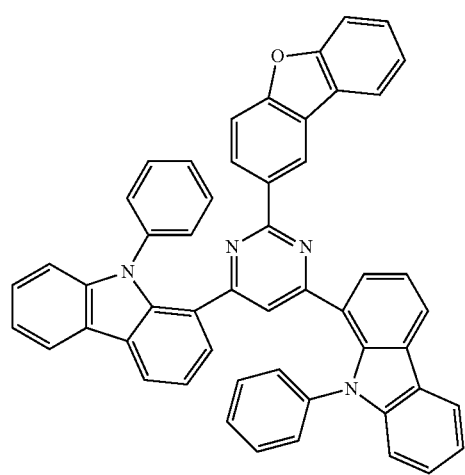
B-29
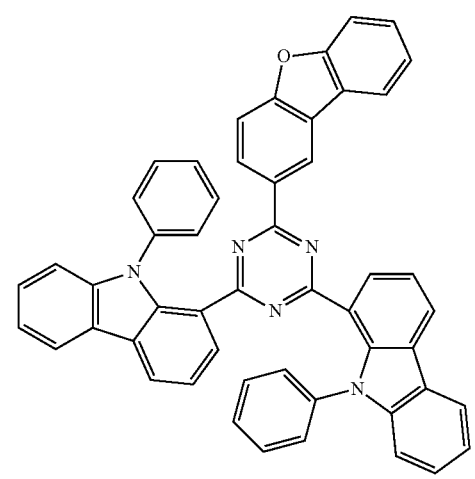
B-30

-continued
B-31
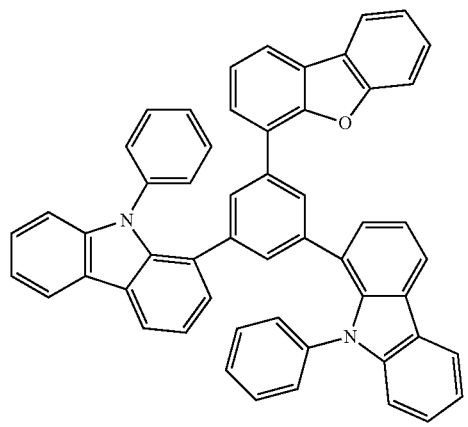
B-32
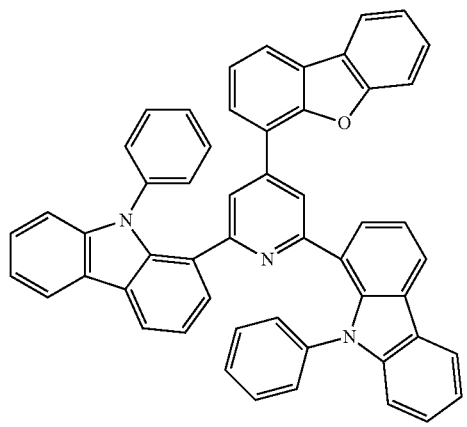
B-33
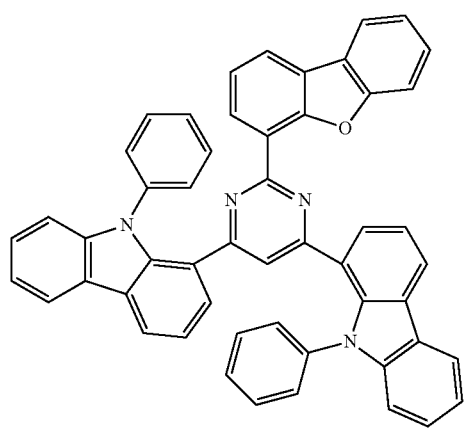
B-34
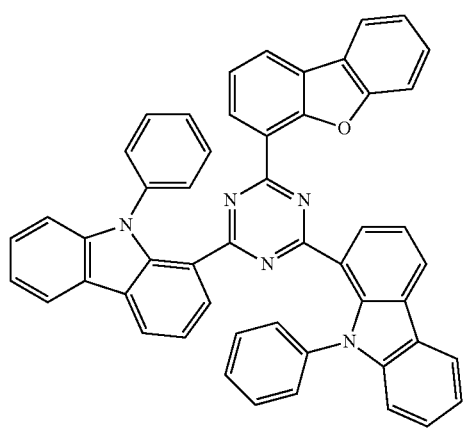
B-35
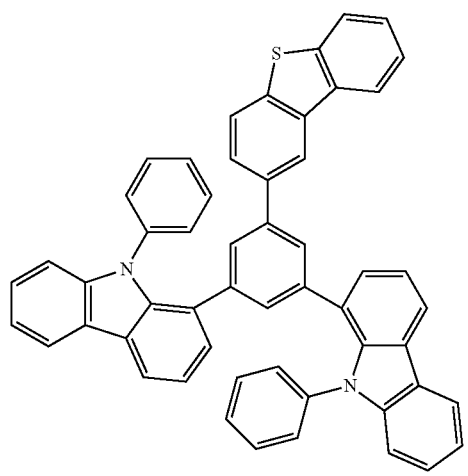
B-36
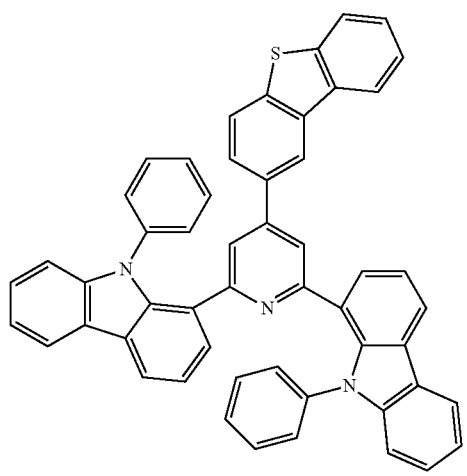

-continued
B-37
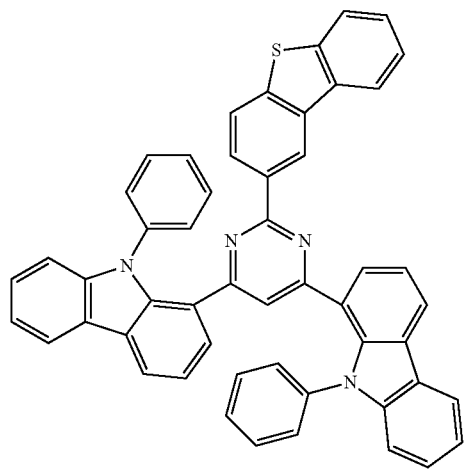
B-38
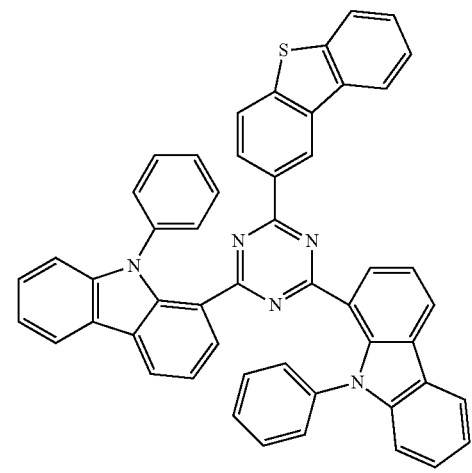
B-39
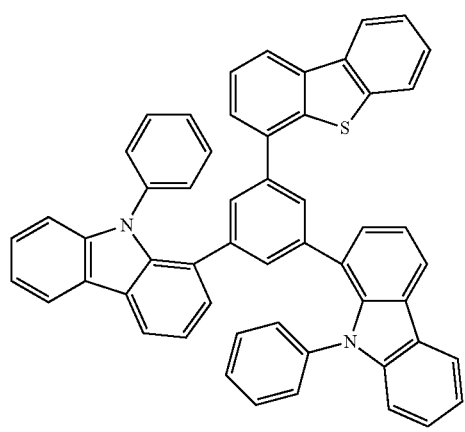
B-40
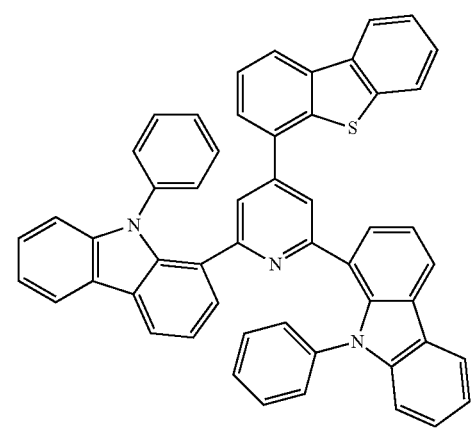
B-41
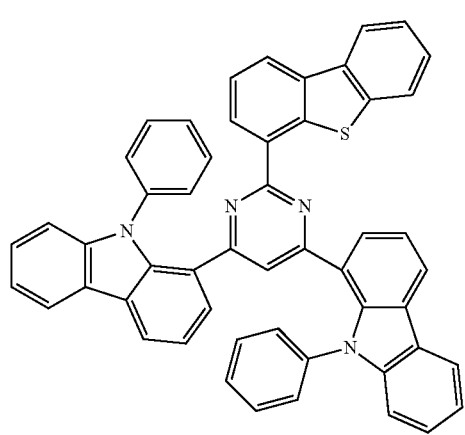
B-42
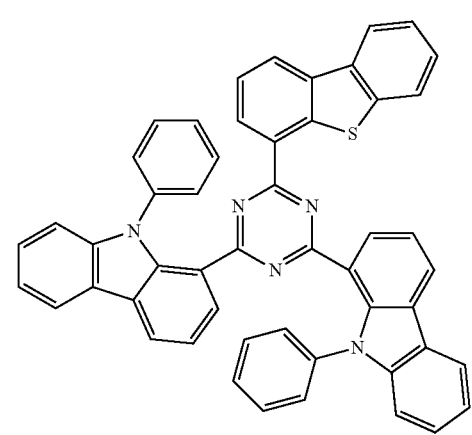

-continued
B-43
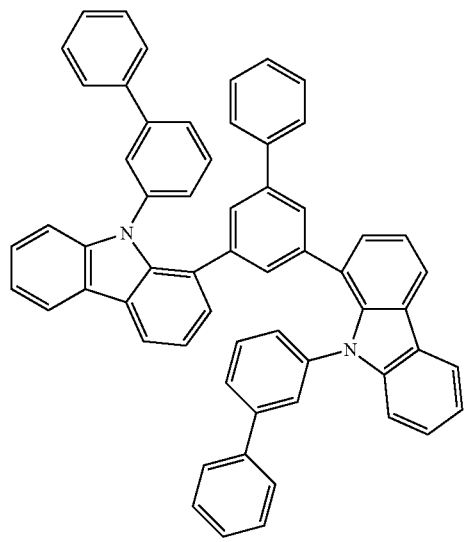
B-44
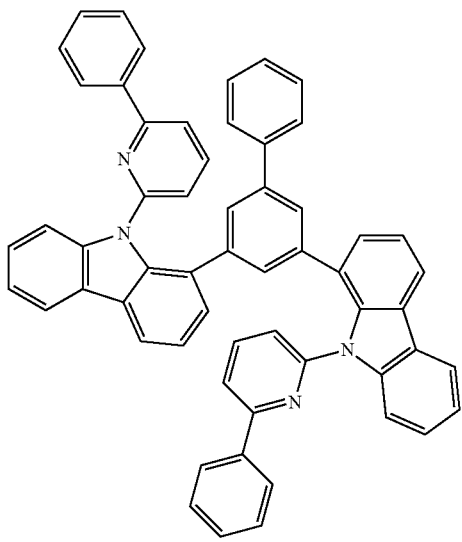
B-45
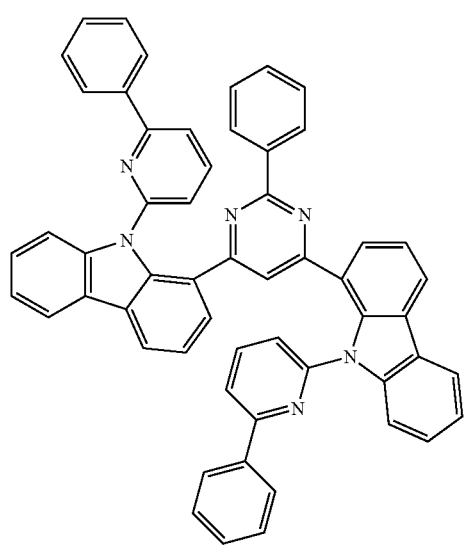
B-46
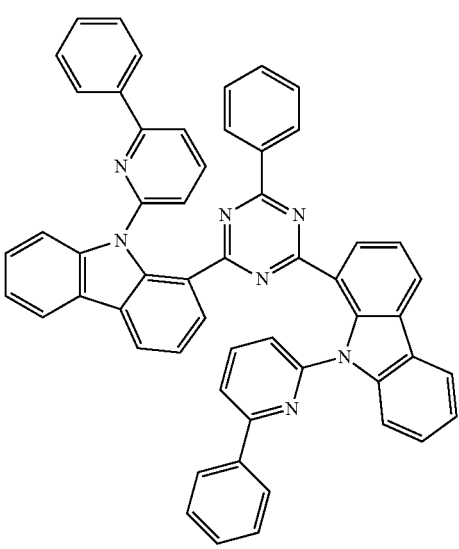
B-47
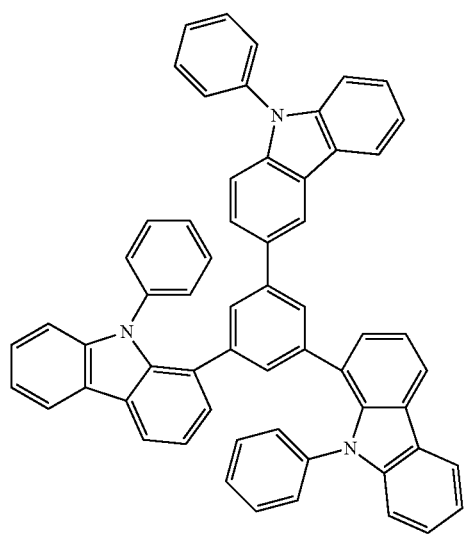
B-48
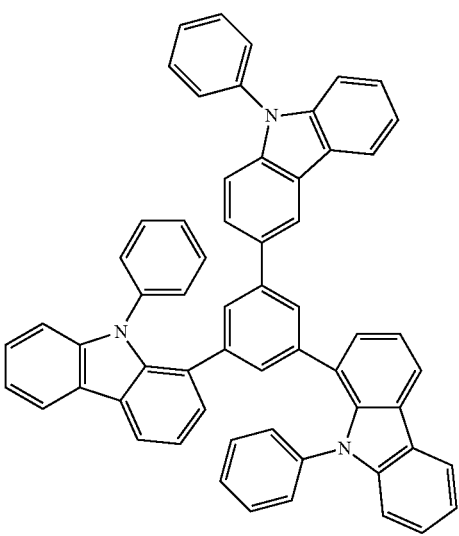

-continued
B-49
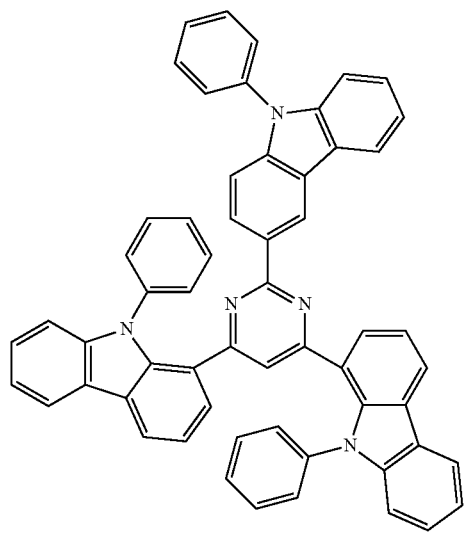
B-50
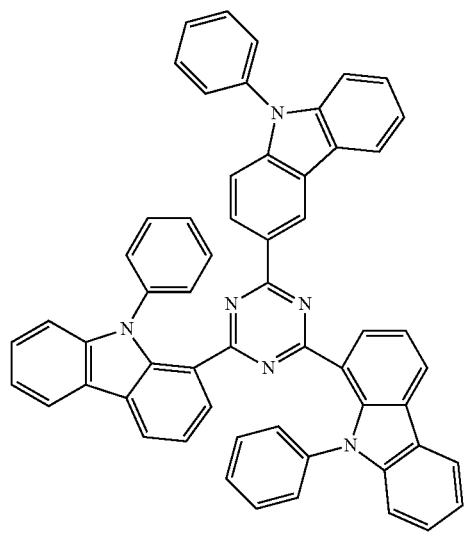
B-51
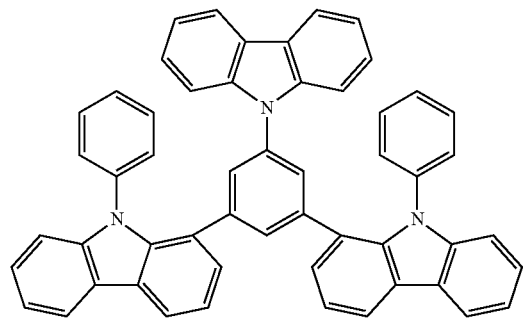
B-52
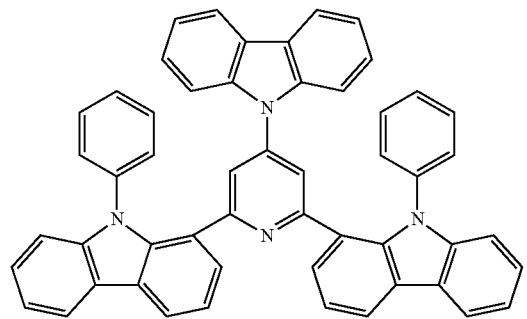
B-53
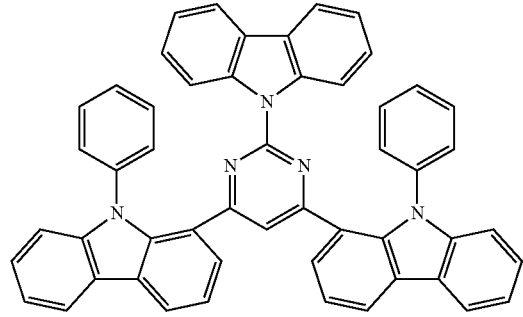
B-54
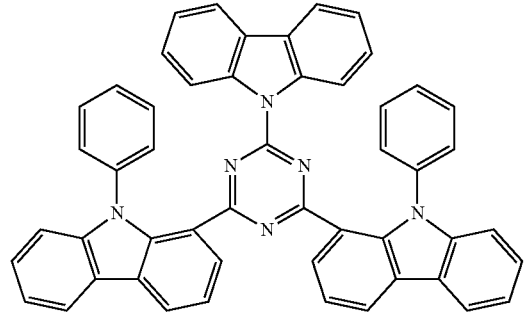
C-1
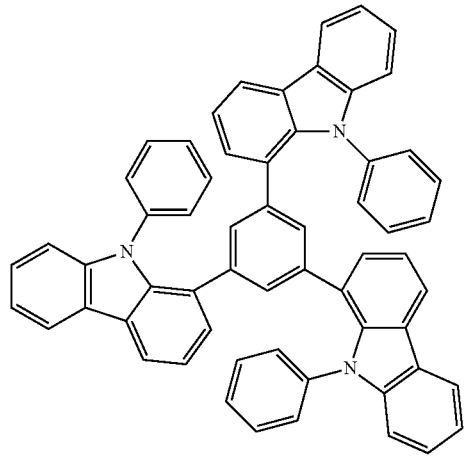
C-2
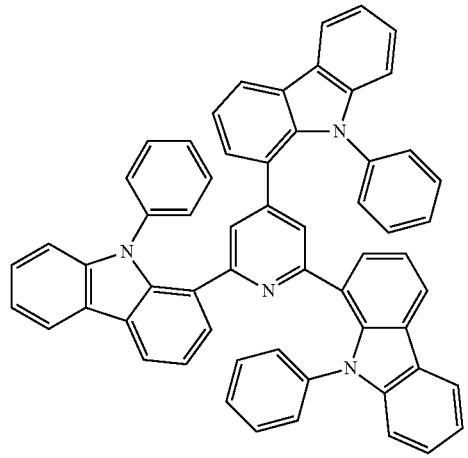

-continued
C-3
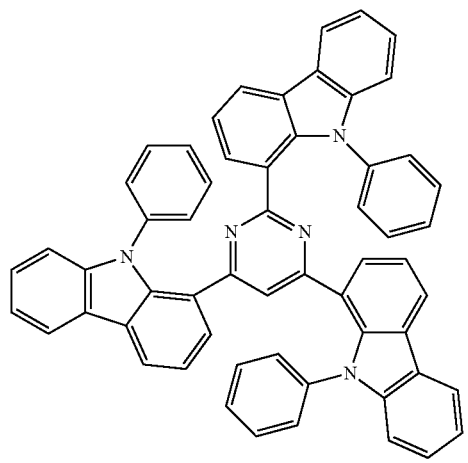
C-4
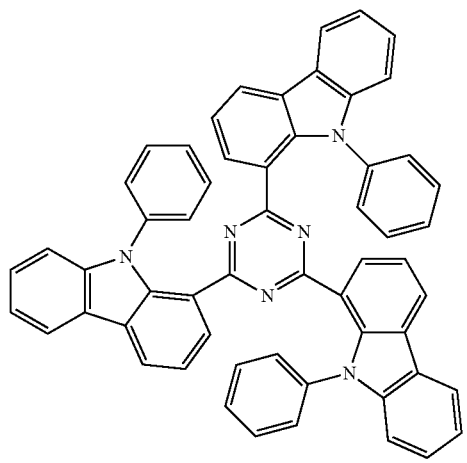
C-5
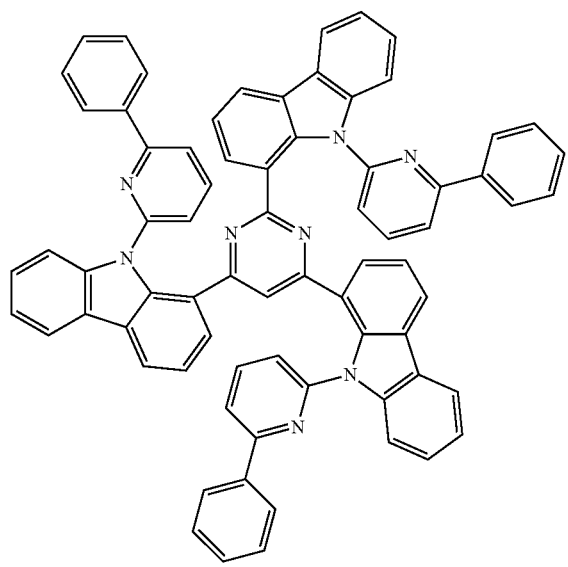
C-6
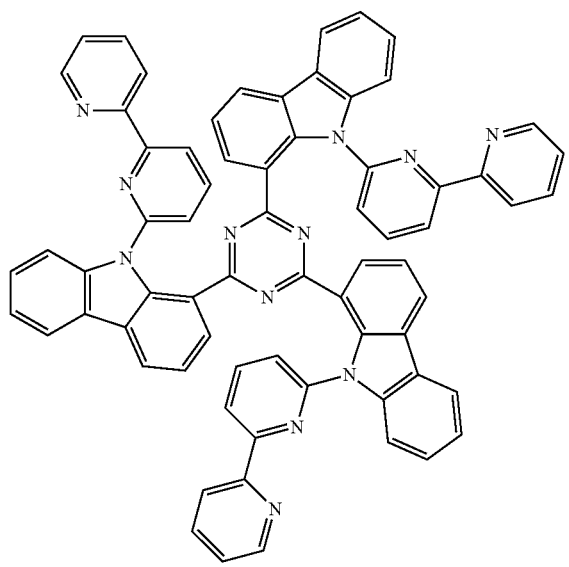
D-1
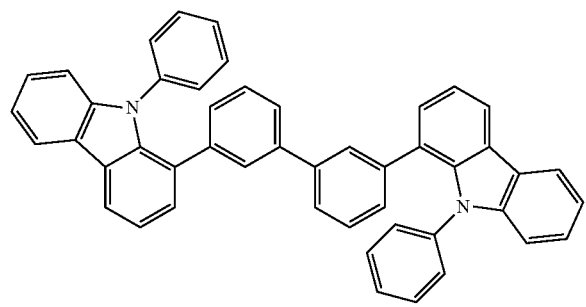
D-2
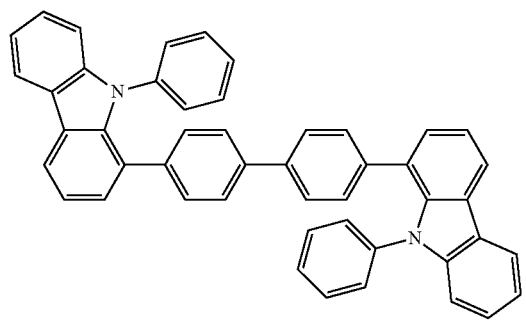

-continued
D-3
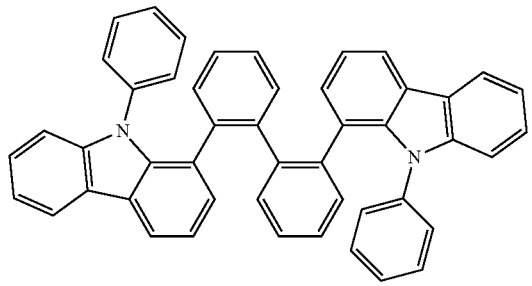
D-4
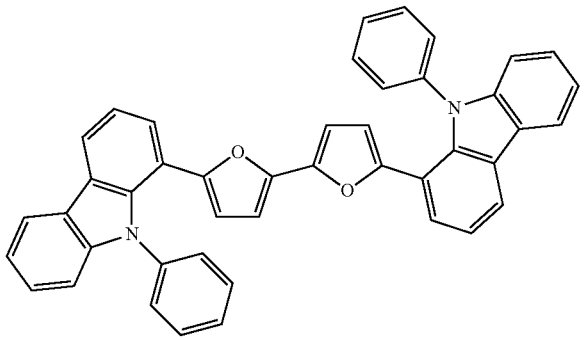
D-5
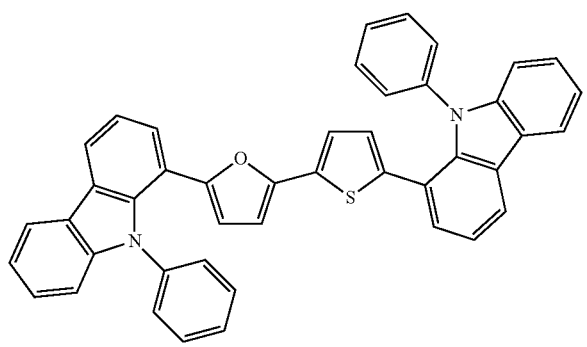
D-6
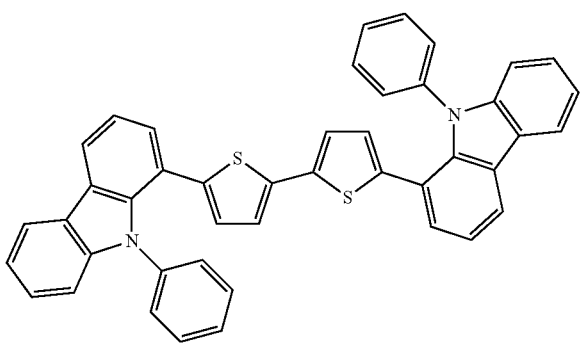
D-7
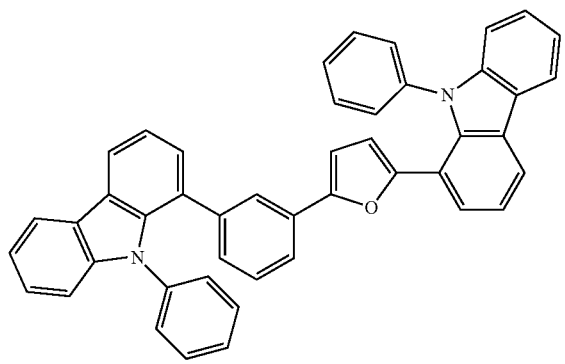
D-8
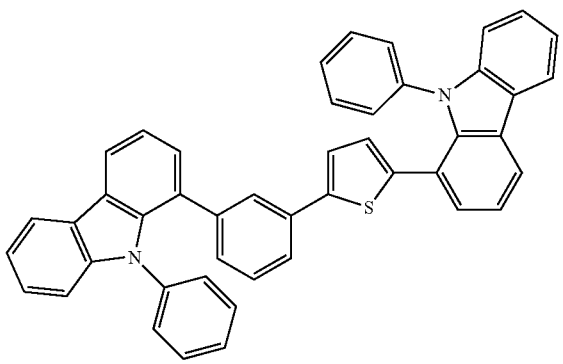
D-9
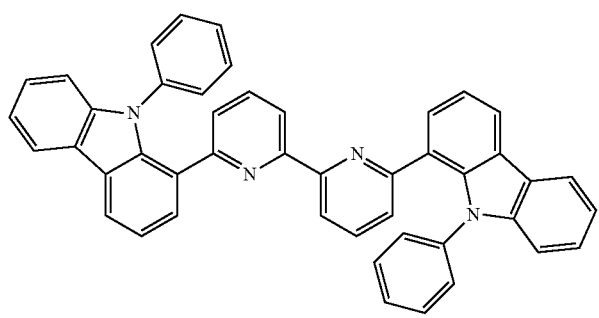
D-10
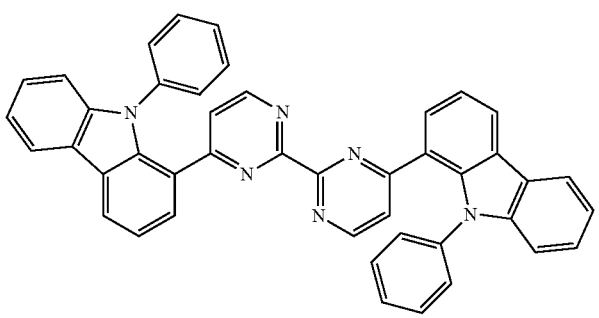

-continued
D-11
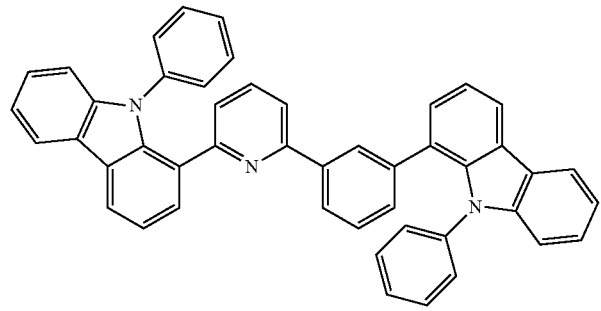
D-12
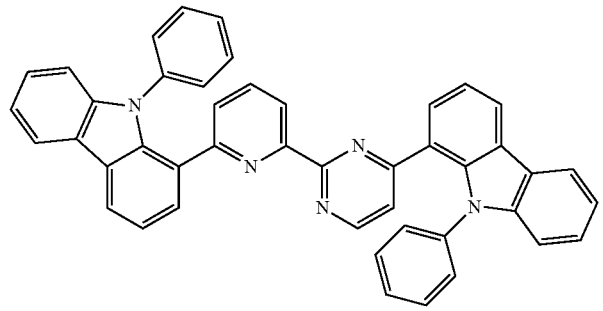
D-13
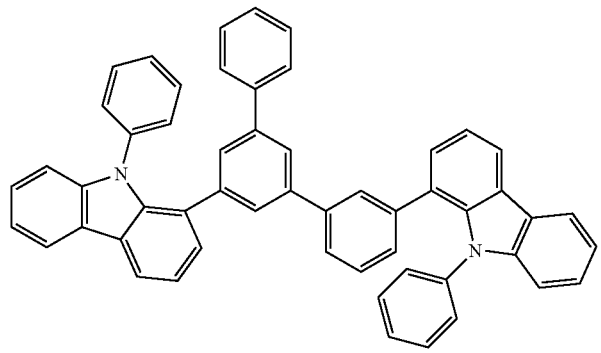
D-14
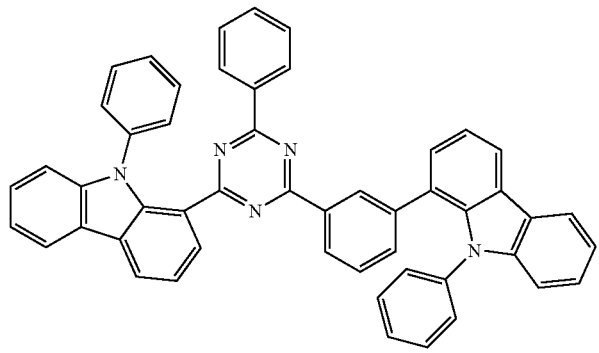
D-15
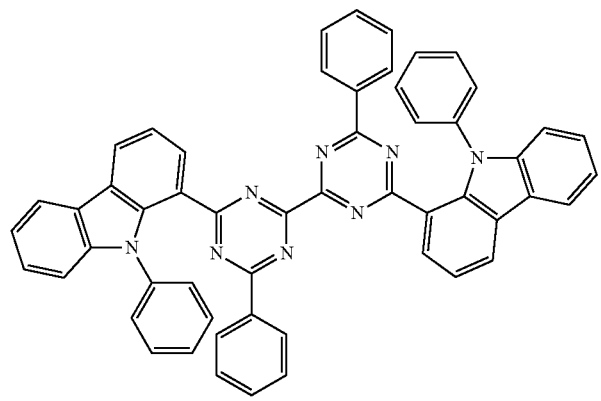
D-16
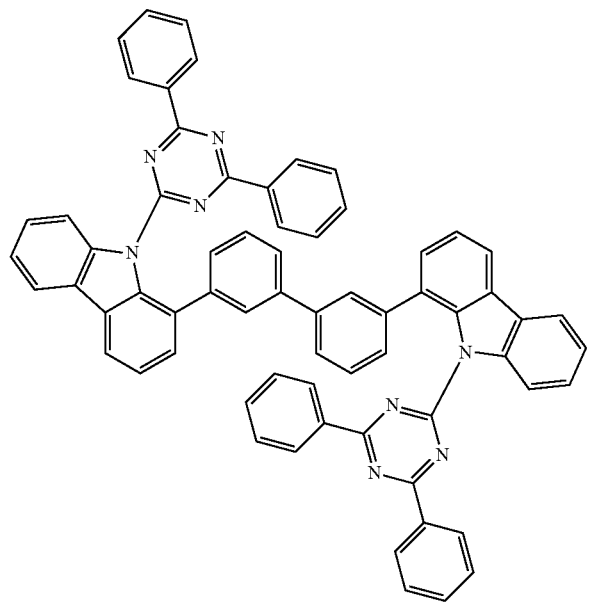

-continued
D-17
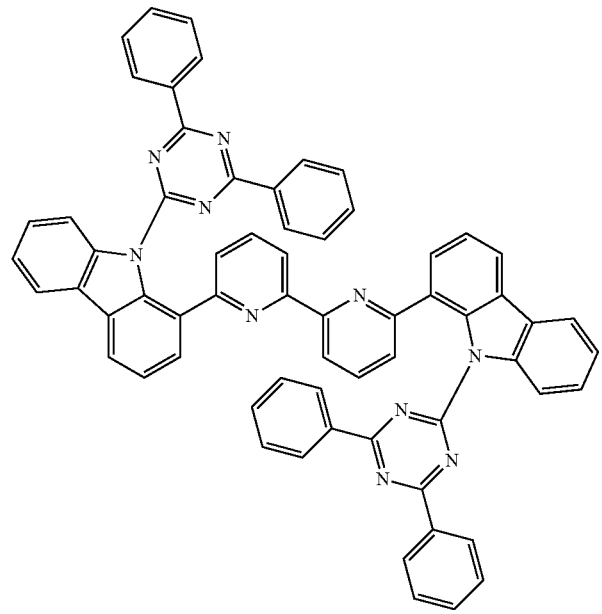
D-18
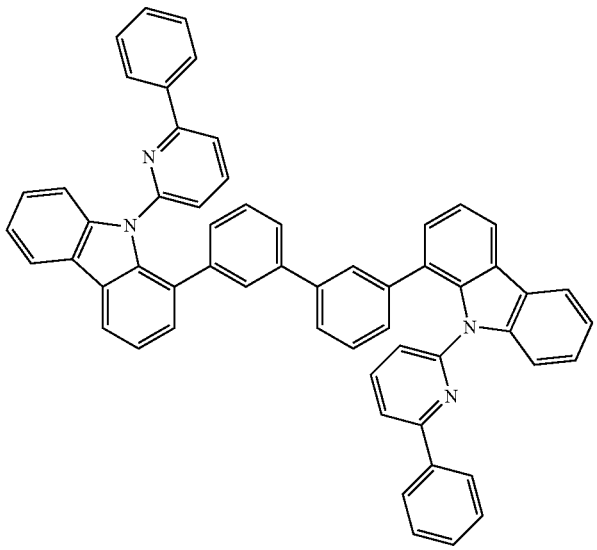
D-19
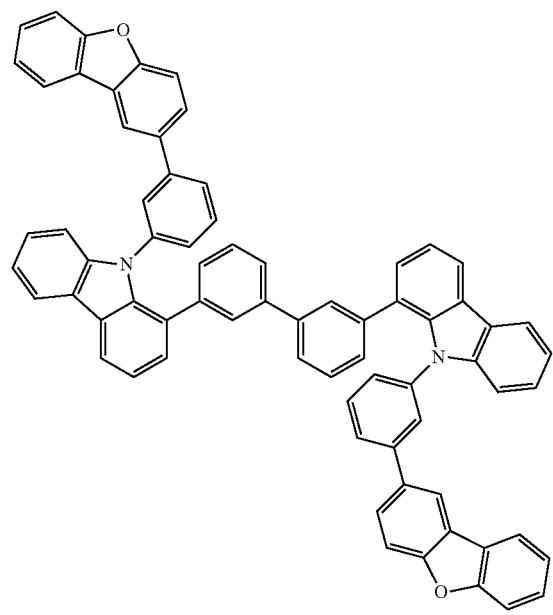
D-20
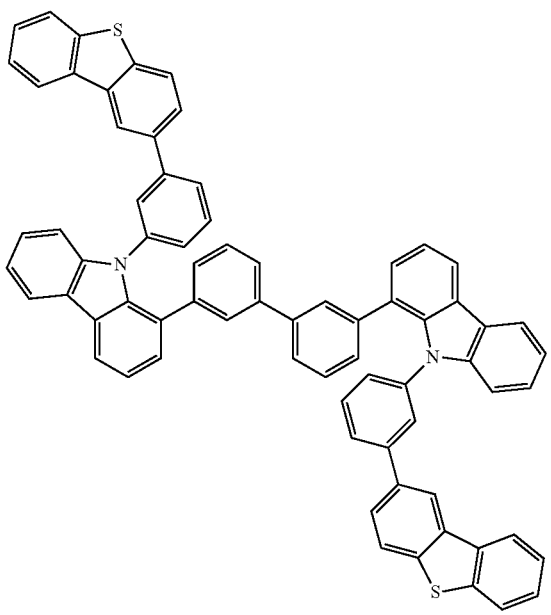

-continued
D-21
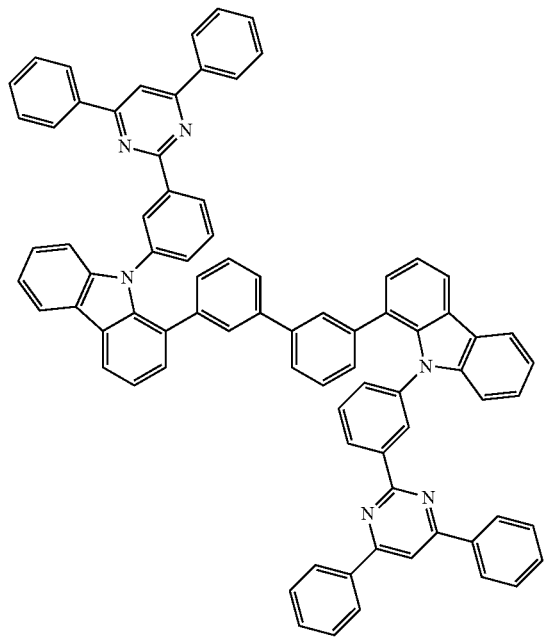
D-22
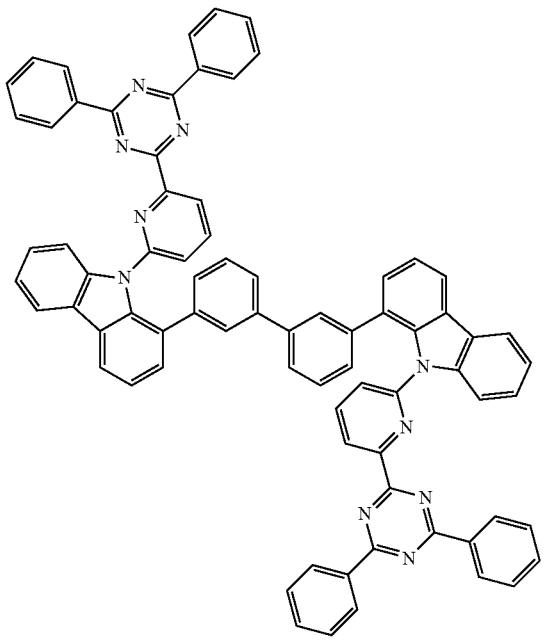
E-1
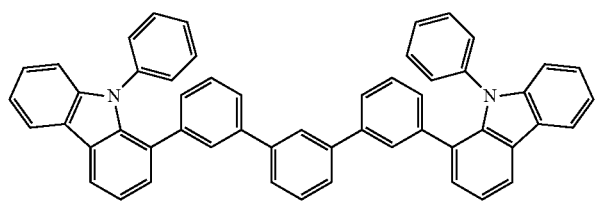
E-2
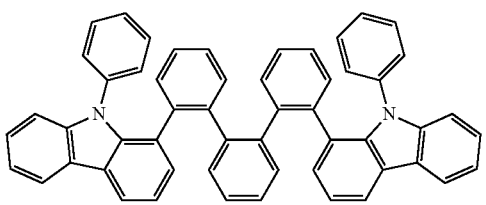
E-3
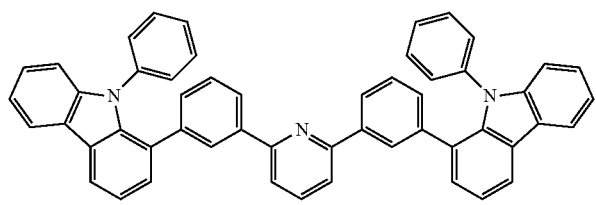
E-4
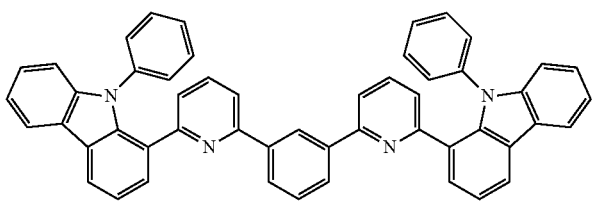
E-5
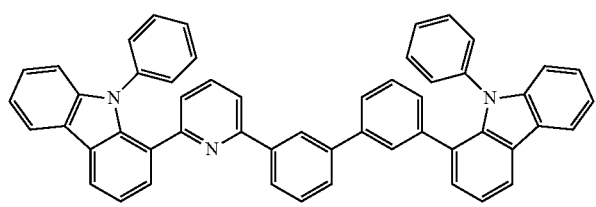
E-6
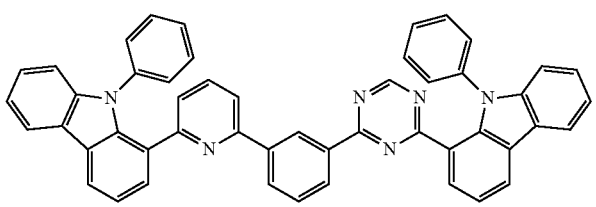
E-7
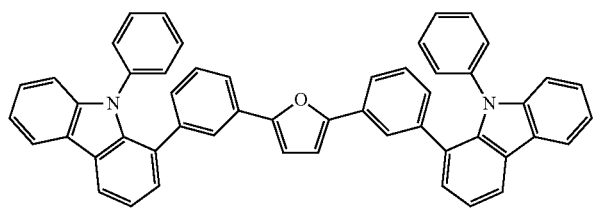
E-8
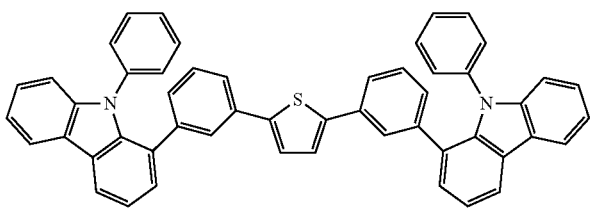

-continued
E-9
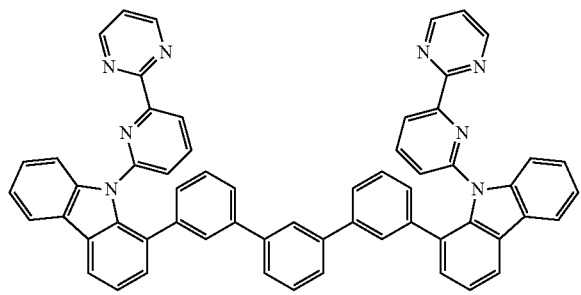
E-10
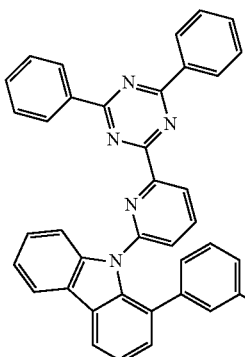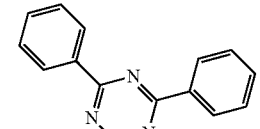
E-11
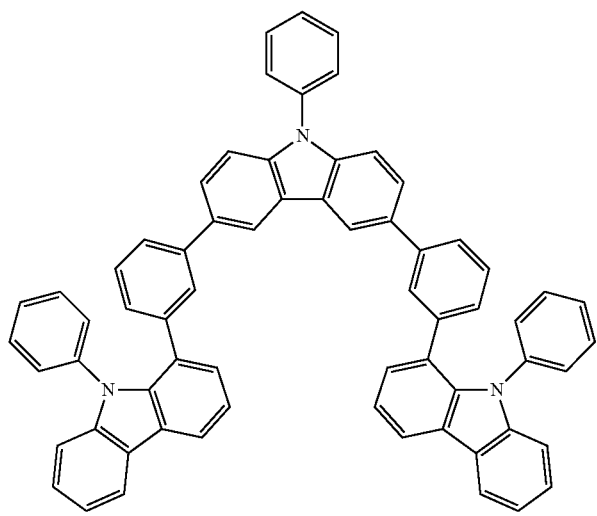
E-12
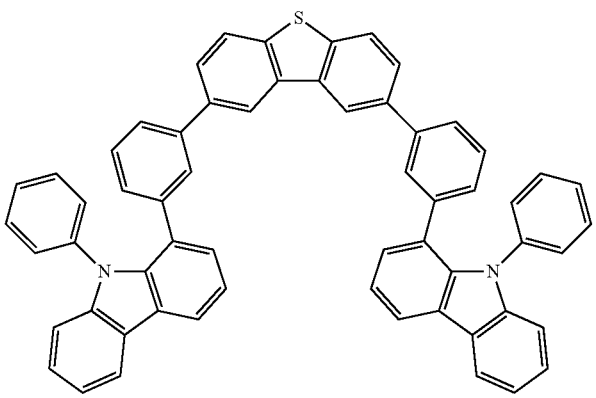
E-13
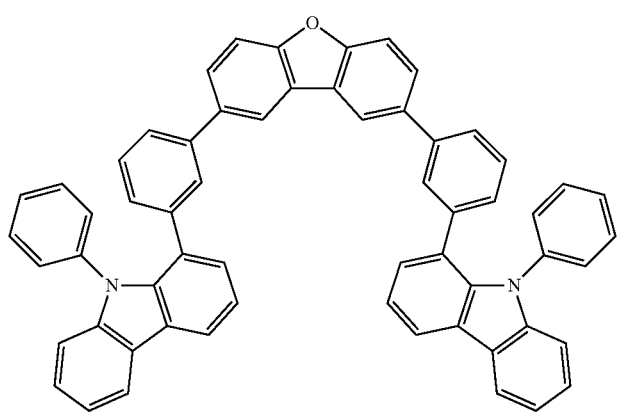

E-14
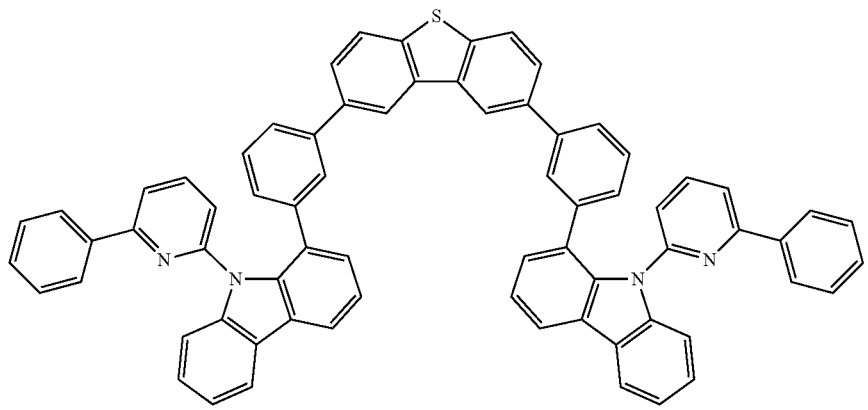
E-15
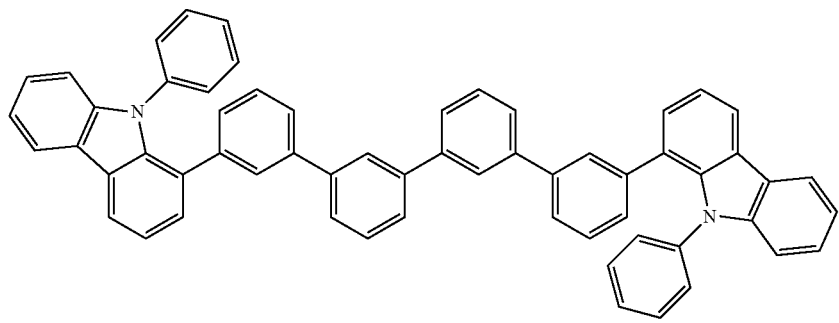
E-16
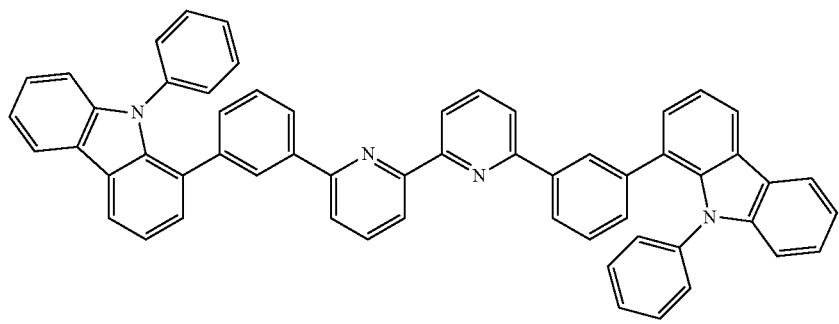
E-17
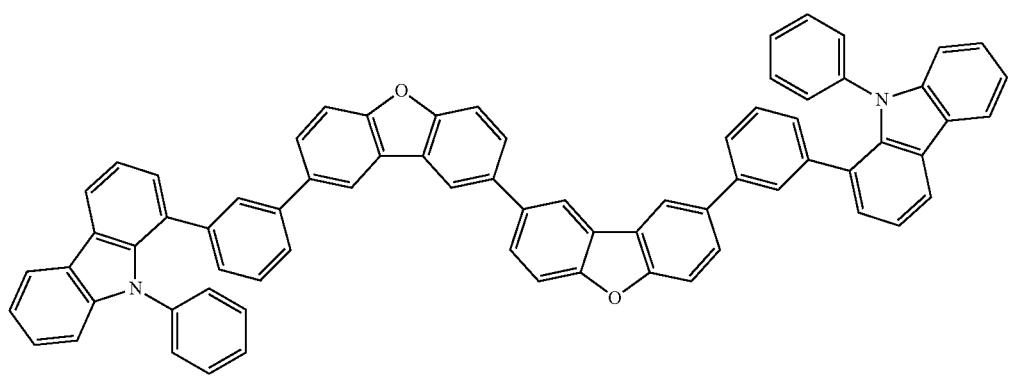

E-18
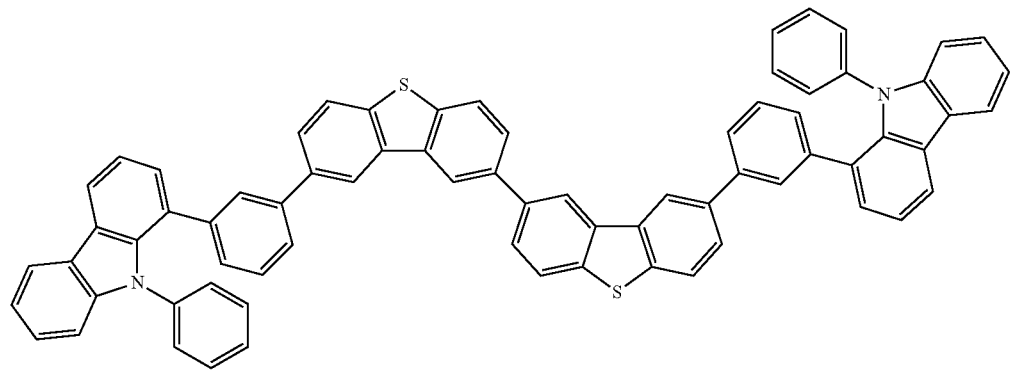
E-19
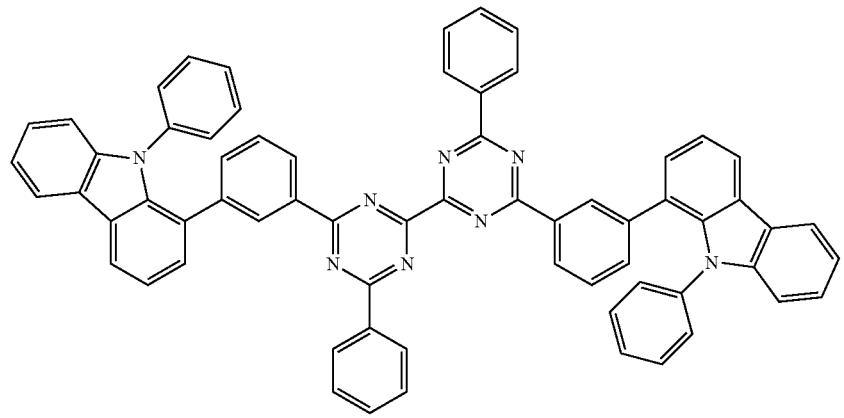
F-1 F-2
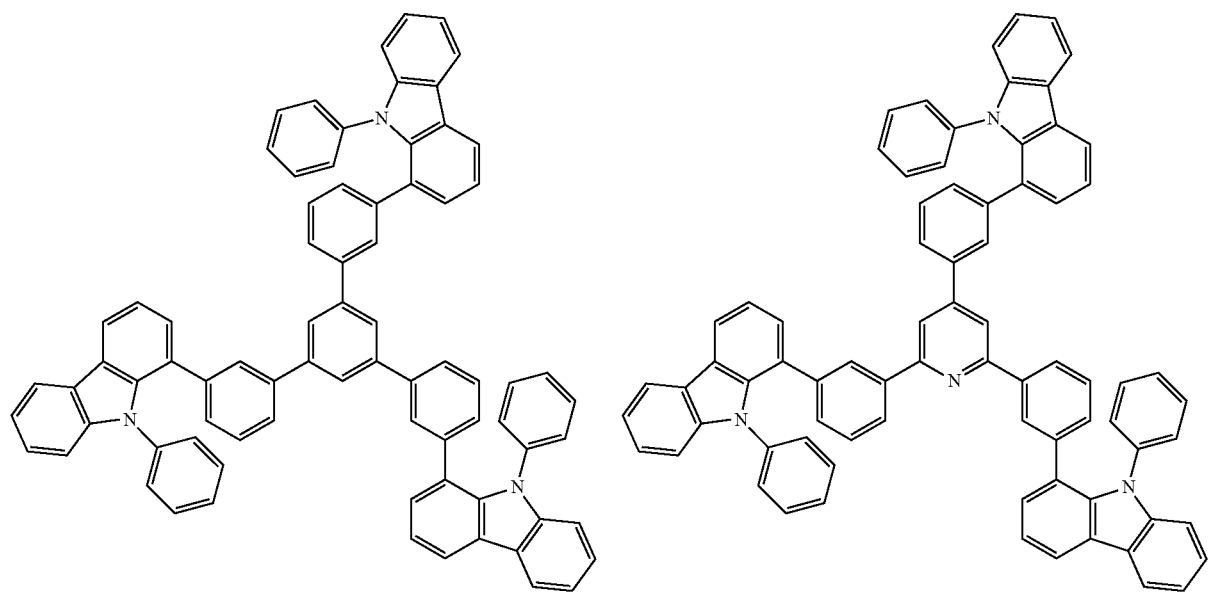

-continued

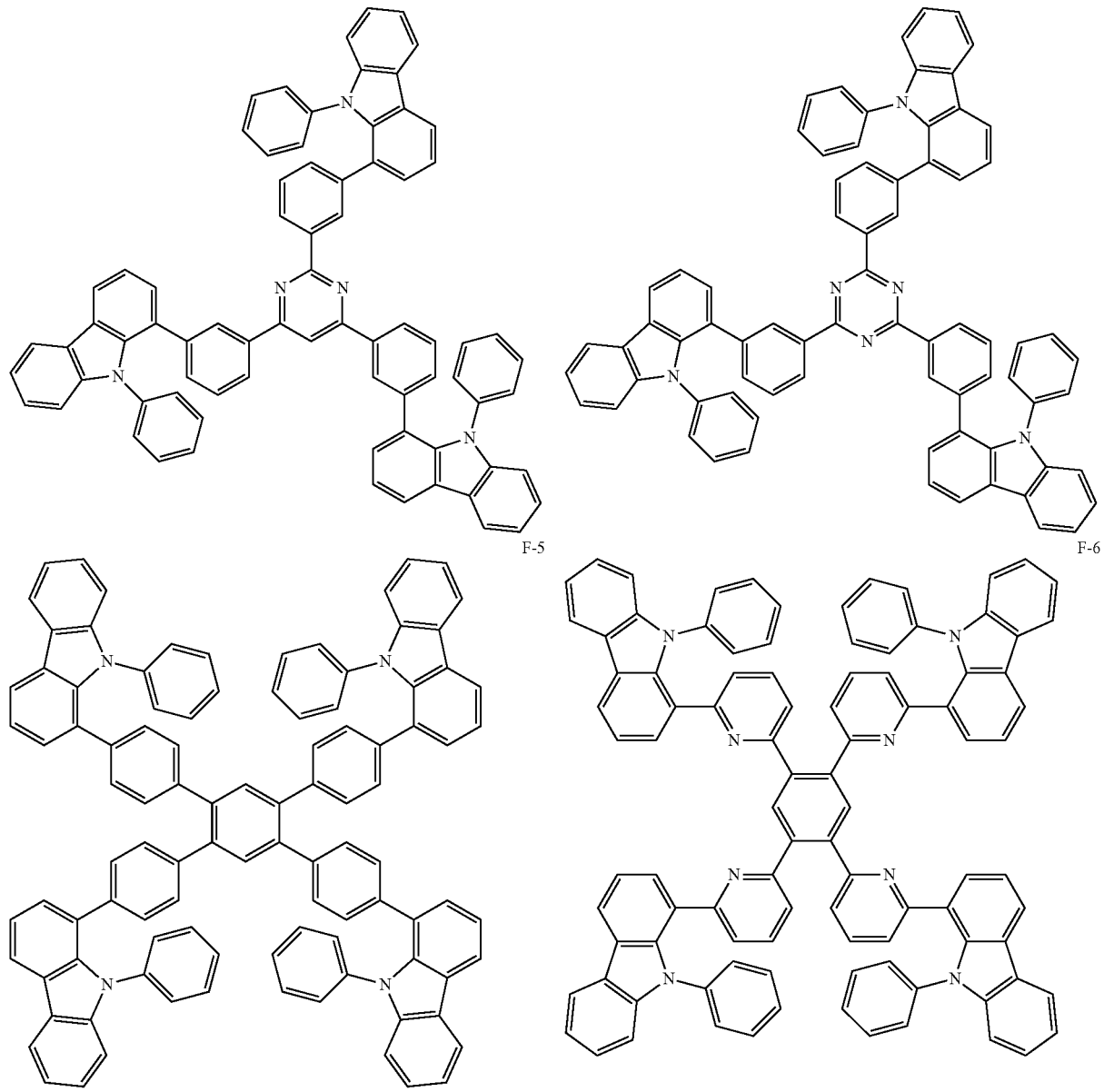

Provided that an organic EL device comprises an anode, a plurality of organic layers, and a cathode piled one upon another on a substrate, incorporation of a compound represented by the aforementioned general formula (1) in at least one of the organic layers helps provide an excellent organic EL device. An organic layer suitable for this purpose is preferably a light-emitting layer, a hole-transporting layer, an electron-transporting layer, or a hole-blocking layer. More preferably, the compound is incorporated as a host material in a light-emitting layer containing a phosphorescent dopant.

An organic EL device according to this invention is explained hereinafter.

The organic EL device of this invention comprises organic layers at least one of which contains a light-emitting layer between an anode and a cathode piled one upon another on a substrate and, further, at least one organic layer contains the aforementioned carbazole compound. Advantageously, the carbazole compound represented by general formula (1) is contained together with a phosphorescent dopant in the light-emitting layer.

The structure of the organic EL device of this invention is explained hereinafter with reference to the drawing, but it will not be limited to the one illustrated in the drawing.

FIG. 1 is the cross section to illustrate an example of the structure of an ordinary organic EL device and the numbers stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The device can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is also possible to add or omit a layer or layers according to the need.

—Substrate—

The organic EL device of this invention is preferably supported by a substrate. There is no specific restriction on the substrate and any of the substrates which have been used customarily in organic EL devices can be used. For example, a substrate made from glass, transparent plastic, or quartz may be used.

—Anode—

The anode of an organic EL device is preferably made from an electrode substance having a high work function (4 eV or more) such as a metal, an alloy, an electrically conductive compound, and a mixture thereof. Examples of the electrode substances of this kind include metals such as Au and electrically conductive transparent materials such as CuI, indium tin oxide (ITO), $SnO_2$, and ZnO. Further, a material that is amorphous and formable into a transparent electrically conductive film such as IDIXO ($In_2O_3$—ZnO) may be used. The anode may be formed by preparing a thin film from any of those electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance that is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred $\Omega/\square$ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal (hereinafter referred to as electron-injecting metal), an alloy, an electrically conductive compound, and a mixture thereof. Examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal that is higher in work function and more stable than the electron-injecting metal is suitable for use as an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of those electrode substances by a method such as vapor deposition and sputtering. The sheet resistance as the cathode is preferably several hundred $\Omega/\square$ or less and the thickness of the film is selected from the range of 10 nm to 5 μm, preferably 50 to 200 nm. Making either the anode or the cathode of an organic EL device transparent or translucent in order to transmit emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to fabricate a device in which both the anode and the cathode display good transmittance properties.

—Light-Emitting Layer—

The light-emitting layer is a phosphorescent light-emitting layer and contains a phosphorescent dopant and a host material. An organic metal complex containing at least one metal selected from ruthenium, rhodium, palladium, silver, rhenium, osmium, iridium, platinum, and gold is suitable for use as a phosphorescent dopant material. The organic metal complexes of this kind are known in the aforementioned prior art technical documents and elsewhere and a suitable organic metal complex may be selected from them and used.

Preferred phosphorescent dopants are complexes containing a noble metal element such as Ir in the center, typically $Ir(ppy)_3$, complexes such as $(Bt)_2Iracac$, and complexes such as (Btp)Ptacac. Examples of these complexes are illustrated below, but are not limited thereto.

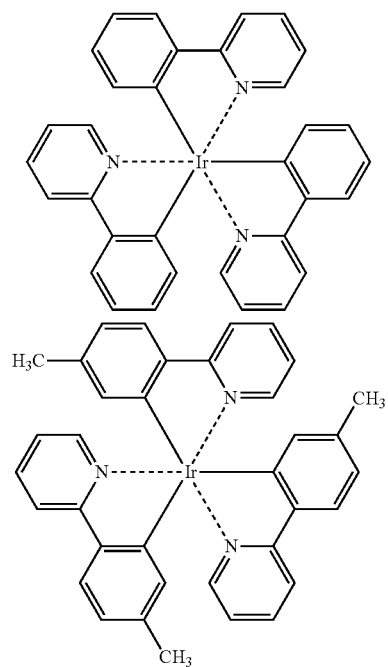

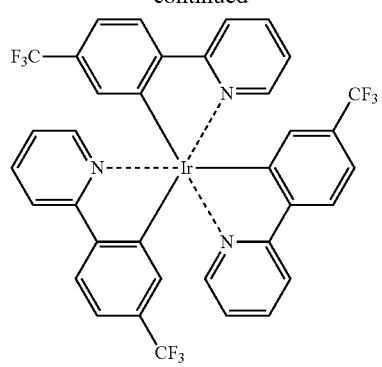
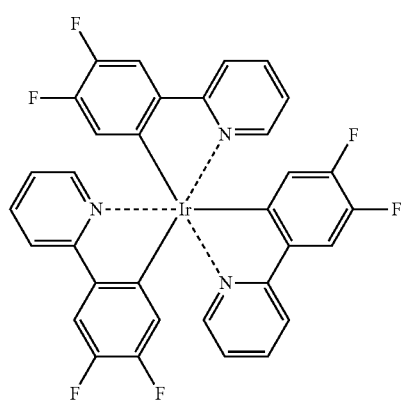
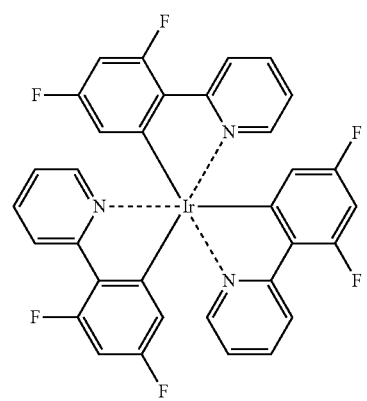
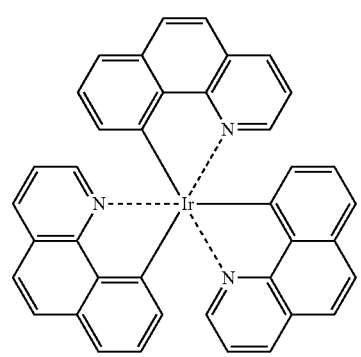
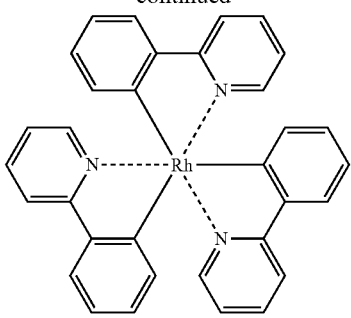
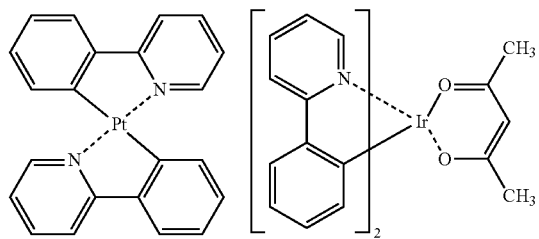
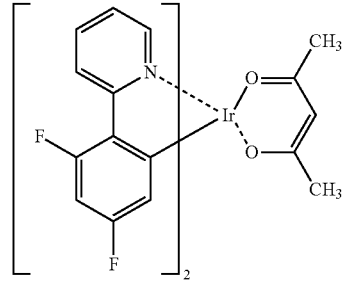
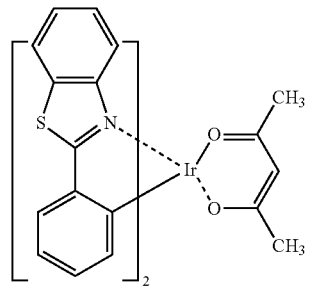
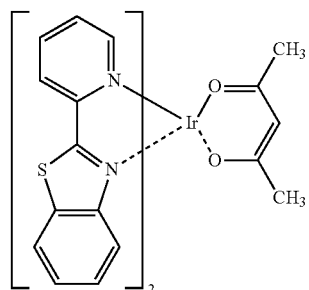
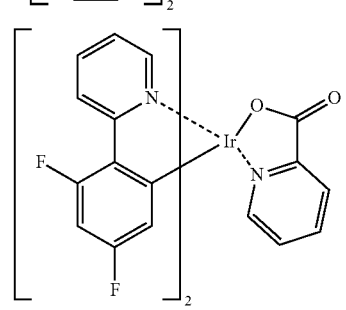

-continued

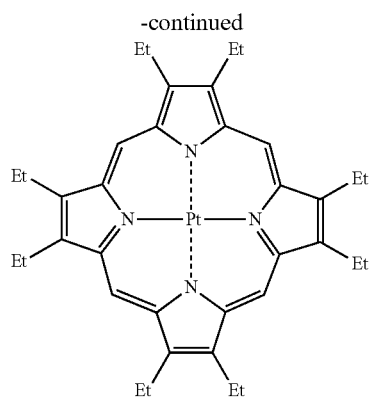

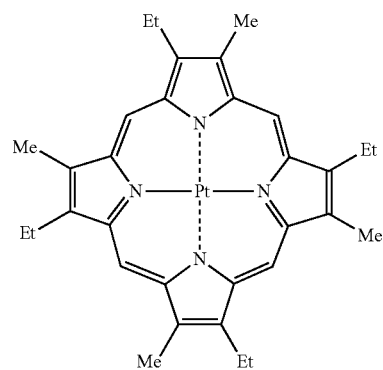

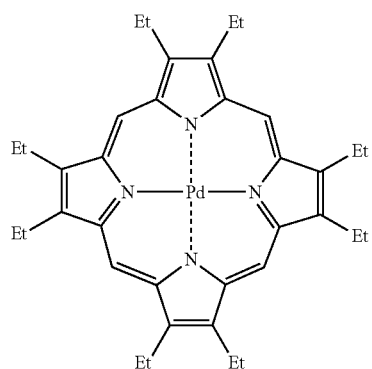

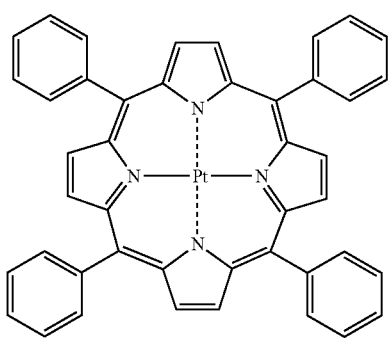

-continued

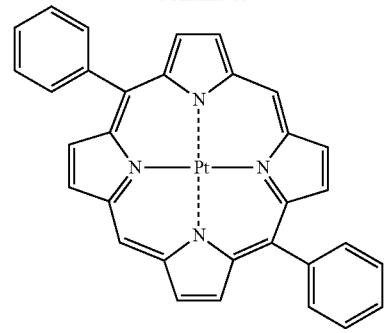

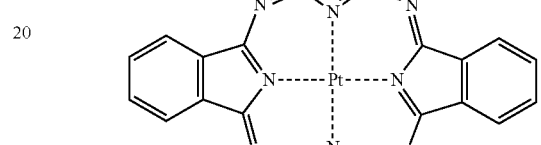

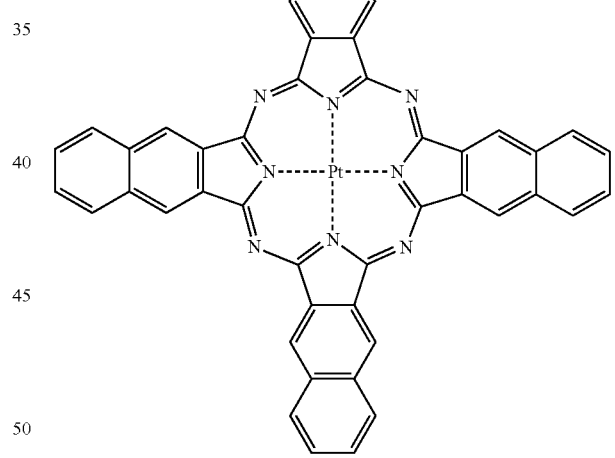

The content of the aforementioned phosphorescent dopant in the light-emitting layer is in the range of 1 to 40 wt %, preferably 5 to 30 wt %.

It is preferable to use a carbazole compound represented by the aforementioned general formula (1) as a host material in the light-emitting layer. However, in the case where the said carbazole compound is used in any of organic layers other than the light-emitting layer, a host material other than the carbazole compound may be used in the light-emitting layer. Further, the carbazole compound may be used together with other host material. Still further, plural kinds of known host materials may be used together.

Among the known host compounds, the ones suitable for use preferably have a hole transport ability and an electron transport ability, can prevent the wavelength of emitted light from shifting to longer wavelengths, and have a high glass transition temperature.

Such known host materials are described in a large number of patent documents and elsewhere and a suitable material may be selected from them. Examples of these host materials include, but are not limited to, indole derivatives, carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer which is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

—Hole-Blocking Layer—

The hole-blocking layer has a function of the electron-transporting layer in a broad sense and is composed of a hole-blocking material that has an extremely poor ability to transport holes while having a function of transporting electrons. The hole-blocking layer can improve the probability of recombination of electrons and holes by transporting electrons while blocking holes.

It is preferable to use a carbazole compound represented by general formula (1) in the hole-blocking layer. However, in the case where the carbazole compound is used in any of other organic layers, a known hole-blocking material may be used instead. Further, any of the materials for the electron-transporting layer to be described later on may be used as a hole-blocking material according to the need.

—Electron-Blocking Layer—

The electron-blocking layer is composed of a material that has an extremely poor ability to transport electrons while having a function of transporting holes and it can improve the probability of recombination of electrons and holes by transporting holes while blocking electrons.

As a material for the electron-blocking layer, any of the materials for the hole-transporting layer to be described later on may be used according to the need. The thickness of the electron-blocking layer is preferably 3 to 100 nm, more preferably 5 to 30 nm.

—Exciton-Blocking Layer—

The exciton-blocking layer is a layer for blocking excitons that are generated by the recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

Examples of a material for the exciton-blocking layer include 1,3-dicarbazolylbenzene (mCP) and bis(2-methyl-8-quinolinolato)-4-phenylphenolatoaluminum(III) (BAlq).

—Hole-Transporting Layer—

The hole-transporting layer is composed of a hole-transporting material that has a function of transporting holes and it may be provided in a single layer or a plurality of layers.

The hole-transporting material has either a property of injecting or transporting holes or a property of constituting a barrier to electrons and it may be either an organic substance or an inorganic substance. It is preferable to use a carbazole compound represented by general formula (1) in the hole-transporting layer. However, it is allowable to select a suitable material from known hole-transporting materials and use it. Examples of known hole-transporting materials suitable for use include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is composed of a material that has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. It is preferable to use a carbazole compound represented by general formula (1) in the electron-transporting layer, but an arbitrary compound may be selected from known compounds and used. Examples of such known compounds include nitro-substituted fluorene derivatives, diphenylquinone derivatives, thiopyran dioxide derivatives, carbodiimide, fluorenylidenemethane derivatives, anthraquinodimethan derivatives, anthrone derivatives, and oxadiazole derivatives. Further, thiadiazole derivatives that are derived from the aforementioned oxadiazole derivatives by substituting a sulfur atom for the oxygen atom of the oxadiazole ring and quinoxaline derivatives that have a quinoxaline ring known as an electron-withdrawing group may be used as electron-transporting materials. Further, polymer materials that contain any of these materials in the polymer chain or polymer materials whose backbone is constituted of any of these materials may be used.

This invention is explained in more detail hereinafter with reference to the examples. However, this invention is not limited to the examples and can be reduced to practice in various modes unless such a practice exceeds the gist of this invention.

A carbazole compound useful as a material for a phosphorescent light-emitting device was synthesized by the routes shown below. The compound numbers in the examples correspond to the numbers assigned to the chemical formulas cited earlier.
SYNTHETIC EXAMPLE 1
Synthesis of Compound A-1
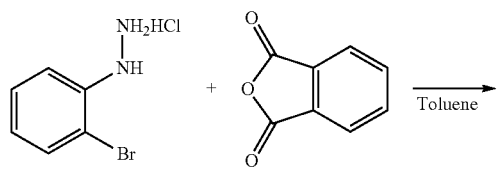
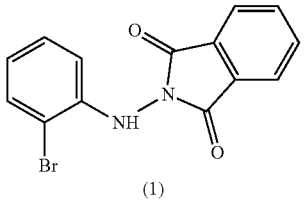
(1)
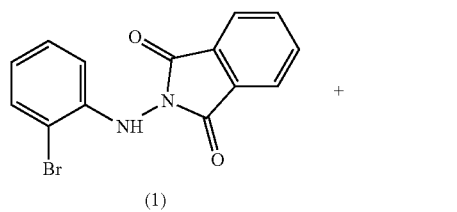
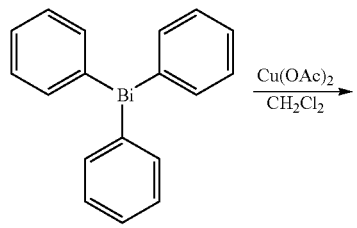
(2)
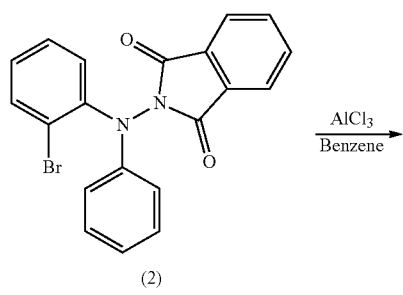
(2)
-continued
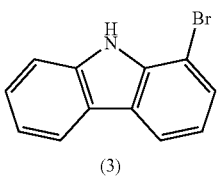
(3)
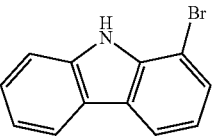 + 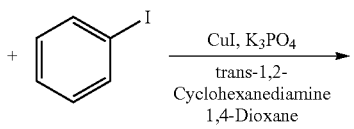
(3)
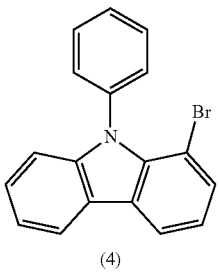
(4)
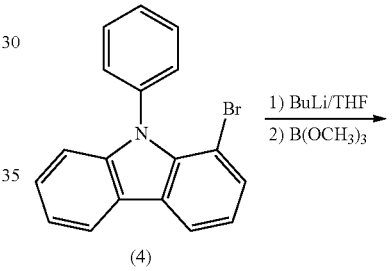
(4)
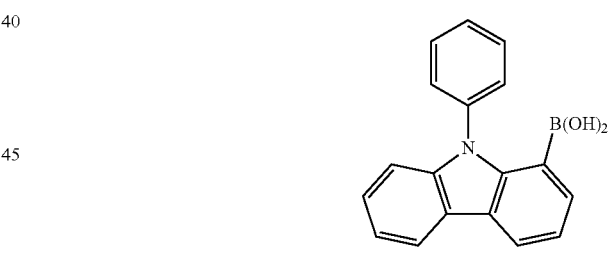
(5)
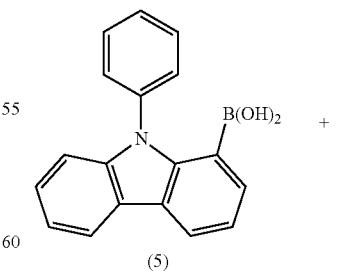
(5)
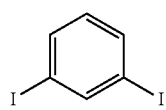 + 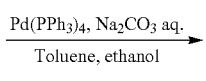

-continued

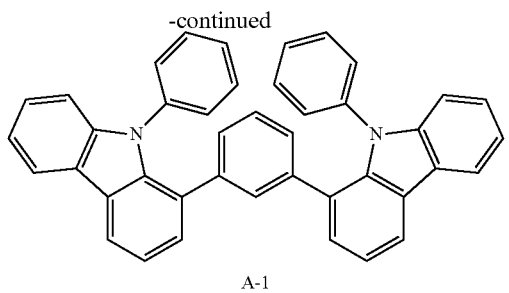

A-1

Under a nitrogen atmosphere, 150.0 g (0.671 mol) of 2-bromophenylhydrazine hydrochloride, 190.0 g (1.3 mol) of phthalic anhydride, and 4,500 ml of toluene were mixed and the mixture was heated at 120° C. with stirring overnight. The reaction solution was cooled to room temperature and the precipitated light yellow solid was collected by filtration. The light yellow solid was purified by reslurrying with application of heat to give 181.0 g (0.57 mol, 71% yield) of Intermediate (1) as a light yellow powder.

Under a nitrogen atmosphere, 126.0 g (0.40 mol) of Intermediate (1), 350.0 g (0.80 mol) of triphenylbismuthine, 108.0 g (0.60 mol) of copper acetate, and 3,000 ml of dehydrated methylene chloride were mixed and the mixture was stirred in an ice bath. To the mixture was slowly added 41.3 ml (0.30 mol) of triethylamine so as to keep the internal temperature from rising above 5° C. and the mixture was heated at 50° C. with stirring overnight. The reaction solution was cooled to room temperature and the precipitated light yellow solid was collected by filtration. The light yellow solid was purified by recrystallization to give 72.0 g (0.18 mol, 45% yield) of Intermediate (2) as a light yellow powder.

Under a nitrogen atmosphere, 30.0 g (0.076 mol) of Intermediate (2) was mixed with 1,500 ml of dehydrated benzene, 50.8 g (0.38 mol) of aluminum chloride was added with stirring at room temperature, and the mixture was stirred at room temperature for 3 hours. To the mixture was added 900 ml of an aqueous solution of sodium hydroxide with stirring. The reaction solution was cooled to room temperature and distilled water (1,000 ml) and toluene (1,000 ml) were added with stirring. The organic layer was washed with distilled water (1,000 ml×3). The organic layer was dried over anhydrous magnesium sulfate, the magnesium sulfate was separated by filtration, and the solvent was distilled off under reduced pressure. The residue was purified by silica gel column chromatography to give 8.0 g (0.033 mol, 43% yield) of Intermediate (3) as a white solid.

Under a nitrogen atmosphere, 21.0 g (0.085 mol) of Intermediate (3), 87.0 g (0.43 mol) of iodobenzene, 65.0 g (0.34 mol) of copper(I) iodide, 72.4 g (0.34 mol) of tripotassium phosphate, and 250 ml of dehydrated 1,4-dioxane were mixed, 38.9 g (0.34 mol) of trans-1,2-cyclohexanediamine was added with stirring at room temperature, and the mixture was heated at 90° C. with stirring for 2 hours. The reaction solution was cooled to room temperature, then filtered through Celite, and the solvent was distilled off under reduced pressure. The residue was purified by silica gel column chromatography to give 17.7 g (0.055 mol, 65% yield) of Intermediate (4) as a colorless liquid.

Under a nitrogen atmosphere, 17.0 g (0.053 mol) of Intermediate (4) was mixed with 300 ml of dehydrated tetrahydrofuran, 41.6 ml (0.069 mol) of n-butyllithium was added at −60° C. with stirring, and the mixture was stirred at −60° C. for 1 hour. Then, 9.4 ml (0.085 mol) of trimethoxyborane was added at −60° C. and the mixture was stirred at room temperature for 1 hour. Thereafter, 50 ml of 2M hydrochloric acid was added, the mixture was stirred for 1 hour, and distilled water (200 ml) and toluene (200 ml) were added with stirring. The organic layer was washed with distilled water (100 ml×3). The organic layer was dried over anhydrous magnesium sulfate, the magnesium sulfate was separated by filtration, and the solvent was distilled off under reduced pressure. The residue was purified by silica gel column chromatography to give 9.1 g (0.032 mol, 60% yield) of Intermediate (5) as a white solid.

Under a nitrogen atmosphere, 4.3 g (0.013 mol) of 1,3-diiodobenzene, 9.0 g (0.031 mol) of Intermediate (5), 0.81 g (0.00052 mol) of tetrakis(triphenylphosphine)palladium(0), 30 ml of toluene, and 6 ml of ethanol were mixed and 20 ml of a 2M aqueous solution of sodium hydroxide was added at room temperature with stirring. The mixture was stirred at 90° C. for 15 hours, then cooled to room temperature, and the organic layer was washed with distilled water (100 ml×3). The organic layer was dried over anhydrous magnesium sulfate, the magnesium sulfate was separated by filtration, and the solvent was distilled off under reduced pressure. The residue was purified by silica gel column chromatography, crystallization, and recrystallization to give 2.2 g (0.0039 mol, 30% yield) of Compound A-1 as a white solid.

Figure 2:
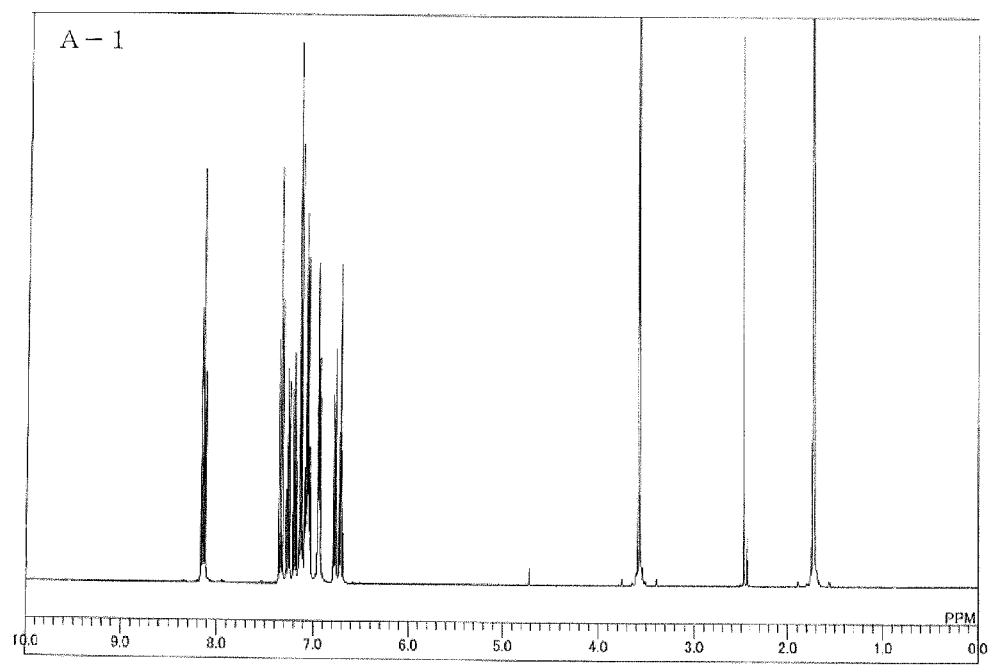
FIG. 2 shows a $^1$H-NMR chart of Compound A-1.

APCI-TOFMS: m/z 561 [M+H]$^+$. The results of $^1$H-NMR measurement (solvent: THF-d$_8$) are shown in FIG. 2.

EXAMPLE 1

The constituent layers were deposited in thin film by the vacuum deposition process at a degree of vacuum of 4.0×10$^{-5}$ Pa one upon another on a glass substrate on which a 110 nm-thick anode had been formed from ITO. First, copper phthalocyanine (CuPc) was deposited on the ITO anode to a thickness of 20 nm. Then, 4,4'-bis[N-(1-naphthyl)-N-phenylamino]biphenyl (NPB) was deposited to a thickness of 20 nm to form a hole-transporting layer. Next, Compound A-1 as a host material and tris(2-phenylpyridine)iridium(III) (Ir(ppy)$_3$) as a dopant were co-deposited on the hole-transporting layer from different deposition sources to a thickness of 30 nm to form a light-emitting layer. At this time, the concentration of Ir(ppy)$_3$ was 10 wt %. Next, BAlq was deposited to a thickness of 10 nm to form a hole-blocking layer. Then, tris(8-hydroxyquinolinato)aluminum (III) (Alq3) was deposited to a thickness of 40 nm to form an electron-transporting layer. Further, lithium fluoride (LiF) was deposited on the electron-transporting layer to a thickness of 1 nm to form an electron-injecting layer. Finally, aluminum (Al) as an electrode was deposited on the electron-injecting layer to a thickness of 70 nm to finish the fabrication of an organic EL device.

The organic EL device thus obtained was connected to an external power source and, upon application of direct current voltage, the device was confirmed to have the luminous characteristics shown in Table 1.

EXAMPLE 2

An organic EL device was fabricated as in Example 1 except that Compound A-8 was used as the host material in the light-emitting layer.

EXAMPLE 3

An organic EL device was fabricated as in Example 1 except that Compound A-19 was used as the host material in the light-emitting layer.

EXAMPLE 4

An organic EL device was fabricated as in Example 1 except that Compound B-31 was used as the host material in the light-emitting layer.

EXAMPLE 5

An organic EL device was fabricated as in Example 1 except that Compound C-4 was used as the host material in the light-emitting layer.

EXAMPLE 6

An organic EL device was fabricated as in Example 1 except that Compound D-1 was used as the host material in the light-emitting layer.

EXAMPLE 7

An organic EL device was fabricated as in Example 1 except that Compound E-3 was used as the host material in the light-emitting layer.

COMPARATIVE EXAMPLE 1

An organic EL device was fabricated as in Example 1 except that mCP was used as the host material in the light-emitting layer.

COMPARATIVE EXAMPLE 2

An organic EL device was fabricated as in Example 1 except that Compound H-1 was used as the host material in the light-emitting layer.

H-1

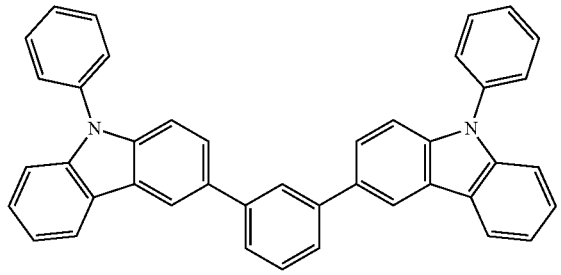

The organic EL devices fabricated in Examples 2 to 7 and Comparative Examples 1 and 2 were evaluated as in Example 1 and they were confirmed to have the luminous characteristics shown in Table 1. Further, the peak emission wavelength of each device is 540 nm and it was identified that light is emitted from Ir(ppy)$_3$.

In Table 1, the values of the luminance, voltage, and luminous efficiency were obtained when the device was driven at 20 mA/cm$^2$.

TABLE 1

|  | Compound | luminance (cd/m$^2$) | Voltage (V) | luminous efficiency (lm/W) |
|---|---|---|---|---|
| Example 1 | A-1 | 14870 | 10.1 | 23.2 |
| 2 | A-8 | 14070 | 9.9 | 22.3 |
| 3 | A-19 | 14160 | 10.1 | 22.0 |
| 4 | B-31 | 13850 | 9.9 | 22.0 |
| 5 | C-4 | 13110 | 9.7 | 21.2 |
| 6 | D-1 | 14560 | 9.8 | 23.3 |
| 7 | E-3 | 14700 | 10.0 | 23.1 |
| Comparative example 1 | mCP | 13620 | 10.8 | 19.9 |
| 2 | H-1 | 10860 | 10.9 | 15.7 |

The device in Example 1 shows improved initial characteristics compared with the devices in Comparative Examples 1 and 2. This indicates that an organic EL device using a carbazole compound composed of two or more carbazole rings linked together via a linking group, each carbazole ring being linked at the position 1 to the linking group and having a specified substituent at the position 9, produces an improvement in the characteristics of the device. Similarly, the devices in Examples 2 to 7 show good characteristics and indicate the superiority of the carbazole compounds represented by general formula (1).

INDUSTRIAL APPLICABILITY

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:
1. An organic electroluminescent device comprising an anode, organic layers, and a cathode piled one upon another on a substrate wherein at least one layer selected from the group consisting of a light-emitting layer, a hole-transporting layer, an electron-transporting layer, and a hole-blocking layer contains a carbazole compound represented by general formula (1);

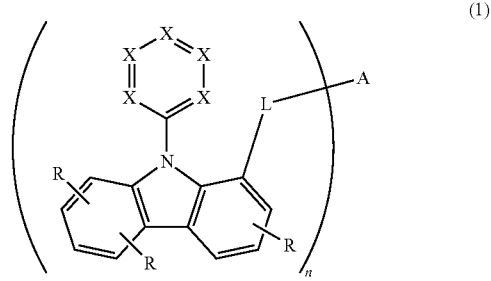

(1)

In general formula (1), each X is independently C—Y or a nitrogen atom and each Y is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 18 carbon atoms; n is an integer of 2 to 4; A is an n-valent aromatic hydrocarbon group of 6 to 50 carbon atoms or an n-valent aromatic heterocyclic group of 3 to 50 carbon atoms; L is a direct bond; each R is independently a hydrogen atom, an alkyl group of 1 to 10 carbon atoms, or a cycloalkyl group of 3 to 11 carbon atoms; however, A cannot have a fused ring structure;

wherein the layer containing the carbazole compound represented by general formula (1) is the light-emitting layer.

2. An organic electroluminescent device as described in claim 1 wherein, in general formula (1), n is 2 or 3.

3. An organic electroluminescent device as described in claim 1 wherein the light-emitting layer contains a phosphorescent dopant.

4. An organic electroluminescent device as described in claim 2 wherein the light-emitting layer contains a phosphorescent dopant.

* * * * *